(12) United States Patent
Penfold

(10) Patent No.: US 11,701,368 B2
(45) Date of Patent: Jul. 18, 2023

(54) UNIT DOSE PHARMACEUTICAL OF A DRY POWDER OF ONE OR MORE GLUCOCORTICOID OR MINERALOCORTICOID FLUDROCORTISONE ACETATE AND/OR TRIAMCINOLONE ACETONIDE COMPRISED IN A SYRINGE

(71) Applicant: EYE CO PTY LTD, Balwyn North (AU)

(72) Inventor: Philip Leslie Penfold, Balwyn North (AU)

(73) Assignee: EYE CO PTY LTD, Balwyn (AU)

( * ) Notice: Subject to any disclaimer, the term of this patent is extended or adjusted under 35 U.S.C. 154(b) by 135 days.

(21) Appl. No.: 16/961,617

(22) PCT Filed: Jan. 9, 2019

(86) PCT No.: PCT/AU2019/000002
§ 371 (c)(1),
(2) Date: Jul. 10, 2020

(87) PCT Pub. No.: WO2019/136512
PCT Pub. Date: Jul. 18, 2019

(65) Prior Publication Data
US 2020/0352963 A1   Nov. 12, 2020

(30) Foreign Application Priority Data

Jan. 10, 2018   (AU) ................. 2018900077

(51) Int. Cl.
*A61K 31/573* (2006.01)
*A61K 9/00* (2006.01)
(Continued)

(52) U.S. Cl.
CPC .......... *A61K 31/573* (2013.01); *A61K 9/0019* (2013.01); *A61K 9/0048* (2013.01);
(Continued)

(58) Field of Classification Search
CPC ........................... A61K 31/573; A61K 9/0019
See application file for complete search history.

(56) References Cited

U.S. PATENT DOCUMENTS

2005/0101582 A1   5/2005  Lyons et al.

FOREIGN PATENT DOCUMENTS

| WO | 1995003807 A1 | 2/1995 |
|---|---|---|
| WO | 2000002564 A1 | 1/2000 |

(Continued)

OTHER PUBLICATIONS

International Search Report and Written Opinion of the International Searching Authority for PCT Application No. PCT/AU2019/000002, dated Feb. 7, 2019 (17 pages).

(Continued)

*Primary Examiner* — Carlos A Azpuru
(74) *Attorney, Agent, or Firm* — Budzyn IP Law, LLC

(57) ABSTRACT

A unit dose pharmaceutical composition comprising 2.0 to 8.0 mg of a dry powder of one or more glucocorticoid or mineralocorticoid or a therapeutically active analogue, derivative, homolog, pharmaceutically acceptable salt or conjugate thereof; wherein the composition is comprised in a syringe is disclosed. The composition may also comprise a a sterile, liquid carrier suitable for direct injection into an eye and/or 0.6 to 0.75% (w/v) of carboxy methyl cellulose (CMC); and 0.015 to 0.04 (w/v) of a surfactant. Also disclosed is a medical device comprising the unit dose pharmaceutical composition, use of the pharmaceutical composition in the treatment of an eye disease or condition or predisposition thereto and a method of treatment of an eye disease or condition or a predisposition thereto in a subject in need thereof including injecting into the eye the pharmaceutical formulation. The injection may comprise an intravitreal and/or suprachoroidal injection.

14 Claims, 7 Drawing Sheets

(51) Int. Cl.
*A61K 9/14* (2006.01)
*A61K 47/38* (2006.01)
*A61K 47/44* (2017.01)
*A61M 5/31* (2006.01)

(52) U.S. Cl.
CPC ................ *A61K 9/14* (2013.01); *A61K 47/38* (2013.01); *A61K 47/44* (2013.01); *A61M 5/31* (2013.01)

(56) References Cited

FOREIGN PATENT DOCUMENTS

| WO | 2005032510 | A1 |   | 4/2005 |
| WO | 2005/09715 | A2 | * | 10/2005 |
| WO | 2005099715 | A2 |   | 10/2005 |
| WO | 2009/114521 | A1 | * | 9/2009 |
| WO | 2009114521 | A1 |   | 9/2009 |
| WO | 2005/099715 | A2 | * | 10/2009 |
| WO | 2015089559 | A1 |   | 6/2015 |
| WO | 2015095624 | A2 |   | 6/2015 |

OTHER PUBLICATIONS

Soikes, Raul, Moving from Vials to Prefilled Syringes: A Project Manager's Perspective, Pharmaceutical Technology Supplement, Sep. 2009, USA.

Song, Michael, "An Introduction To Prefilled Syringe Selection—Needle-Free and Dual-Chamber Devices", https://www.pharmaceuticalonline.com/doc/an-introduction-to-prefilled-syringe-selection-needle-free-and-dual-chamber-devices-0001.html, Date of search, Oct. 21, 2019.

Australian Product Information: KENACORT®-A 40 (sterile triamcinolone acetonide suspension USP) 40 mg in 1 mL injection ampoule, Data Sheet, (Undated), Australia.

* cited by examiner

11-DC

DCS

DCSA

FLU (micronised)

TA micronised (obtained previously at Monash)

UNIT DOSE PHARMACEUTICAL OF A DRY POWDER OF ONE OR MORE GLUCOCORTICOID OR MINERALOCORTICOID FLUDROCORTISONE ACETATE AND/OR TRIAMCINOLONE ACETONIDE COMPRISED IN A SYRINGE

FIELD OF THE INVENTION

THIS INVENTION described herein relates generally to a medical device, pharmaceutical composition and method for making a pharmaceutical composition for treating an eye disease or condition including a diabetic eye disease and an ocular tumour. In particular, the invention is directed to a medical device and pharmaceutical composition comprising a unit dose formulation of one or more glucocorticoid or mineralocorticoid and a method of making such a pharmaceutical composition.

BACKGROUND OF THE INVENTION

Triamcinolone acetonide (TA) is a synthetic corticosteroid indicated for various diabetic and neovascular retinal disease and inflammatory conditions which are unresponsive to topical corticosteroids. Triamcinolone acetonide has been used as a mono-therapy and co-therapy for various back of eye conditions and is also indicated for visualisation during vitrectomy. Since the initial report of its use in humans to treat exudative macular degeneration (Penfold, P. L. et al., "Exudative macular degeneration and intra vitreal triamcinolone. A pilot study." Aust. N.Z.J. Ophthalmol. 1995: 23(4):293-298), triamcinolone acetonide is now widely used for treatment of diabetic retinopathy, uveitis and choroidal neovascularisation associated with age-related macular degeneration.

Diabetic macular edema (DME) is the leading cause of visual loss in diabetic retinopathy. Intravitreal triamcinolone acetonide has been used successfully to improve visual acuity while significantly reducing DME and also to reduce central macular thickness. Although such use is considered off-label in the US, many retina specialists advocate using intravitreal triamcinolone acetonide in primary treatment of refractory DME.

A proposed mechanism of action is that TA increases the levels of tight-junction proteins and thus diminishes vessel leakage and angiostatic actions through vascular endothelial growth factor (VEGF) inhibition. Despite having great potential, intravitreal triamcinolone acetonide carries considerable risks including cataract formation and glaucoma.

TA is available in various different formulations. A study evaluated the rate of sterile endophthalmitis (SE) following intravitreal injection of three different formulations of TA (Dodwell D. G. et al., Sterile endophthalmitis rates and particle size analyses of different formulations of triamcinolone acetonide. Clin. Ophthalmol: 2015; 9: 1033-1040). The three formulations evaluated were Triescence®, Kenalog®-40 and preservative-free TA. Four cases of SE were observed following treatment with Triescence®. One case of SE was observed following treatment with the preservative-free TA and no cases were observed following treatment with Kenelog®-40. Triescence has the smallest particle size and highest particle load (number of particles injected).

There remains a need for alternative formulations.

SUMMARY OF THE INVENTION

The present invention has arisen after the inventors discovered an improved medical device, improved pharmaceutical composition and an improved method for making a pharmaceutical composition for the treatment of an eye disease and/or condition or predisposition thereto.

In a broad form, the invention relates to a medical device comprising a unit dose pharmaceutical composition, a unit dose pharmaceutical composition, a method for making a unit dose pharmaceutical composition and a unit dose pharmaceutical composition for the treatment of an eye disease or condition or predisposition thereto.

In a first aspect, the present invention is broadly directed to a unit dose pharmaceutical composition comprising: 2.0 to 8.0 mg of a dry powder of one or more glucocorticoid or mineralocorticoid or a therapeutically active analogue, derivative, homolog, pharmaceutically acceptable salt or conjugate thereof; wherein the unit dose pharmaceutical composition is comprised in a syringe.

In a second aspect, the present invention is broadly directed to a medical device comprising a unit dose pharmaceutical composition comprising: 2.0 to 8.0 mg of a dry powder of one or more glucocorticoid or mineralocorticoid or a therapeutically active analogue, derivative, homolog, pharmaceutically acceptable salt or conjugate thereof; wherein the unit dose pharmaceutical composition is comprised in a syringe.

The composition of the first aspect or device of the second aspect may further comprise a sterile, liquid carrier suitable for direct injection into an eye. The dry powder may be dissolved or suspended into the sterile, liquid carrier.

In a third aspect, the present invention is broadly directed to a unit dose pharmaceutical composition comprising: 2.0 to 8.0 mg of one or more glucocorticoid or mineralocorticoid or a therapeutically active analogue, derivative, homolog, pharmaceutically acceptable salt or conjugate thereof; 0.6 to 0.75% (w/v) of carboxy methyl cellulose (CMC); and 0.015 to 0.04 (w/v) of a surfactant; wherein the unit dose pharmaceutical composition is comprised in a syringe.

In a fourth aspect, the present invention is broadly directed to a medical device comprising a unit dose pharmaceutical composition comprising: 2.0 to 8.0 mg of one or more glucocorticoid or mineralocorticoid or a therapeutically active analogue, derivative, homolog, pharmaceutically acceptable salt or conjugate thereof; 0.6 to 0.75% (w/v) of carboxy methyl cellulose (CMC); and 0.015 to 0.04 (w/v) of a surfactant; wherein the unit dose pharmaceutical composition is comprised in a syringe.

In a fifth aspect, the present invention provides the unit dose pharmaceutical composition or the medical device of any one of the first, second, third or fourth aspects for use or when used in the treatment of an eye disease or condition or predisposition thereto.

In a sixth aspect, the present invention provides a method of treatment of an eye disease or condition or a predisposition thereto in a subject in need thereof, the method including injecting into said eye the unit dose pharmaceutical formulation of any one of the first, second, third or fourth aspects. The injection may comprise intravitreal and/or suprachoroidal injection.

According to the sixth aspect, the injection may use a double-barrelled syringe and a first barrel and a second barrel are injected substantially simultaneously.

In a seventh aspect, the present invention provides the use of the unit dose pharmaceutical composition of any one of the first to fourth aspects for the manufacture of a medicament for the therapeutic and/or prophylactic treatment of an eye disease or condition.

In an eighth aspect, the present invention provides a syringe comprising the unit dose pharmaceutical composition of the first or third aspects.

In one embodiment of any one of the above aspects, the syringe comprises a 25 to 30 gauge. The gauge may comprise 25, 26, 27, 28, 29 or 30 gauge. In a particular embodiment the gauge comprises 27. The syringe may comprise a 27 G thin wall needle.

The syringe according to any one of the above aspects may comprise a volume of 0.25 to 0.75 ml. The volume may comprise 0.25, 0.30, 0.35, 0.40, 0.45, 0.50, 0.55, 0.60, 0.65, 0.70 or 0.75 ml. In a preferred embodiment volume comprises 0.50 ml.

The syringe according to any one of the above aspects may be a double-barrelled syringe. The first barrel may comprise the pharmaceutical composition of the first or second aspect and the second barrel may comprise another medicament. The another medicament may comprise an anti-VEGF (anti-Vascular Endothelial Growth Factor). The anti-VEGF may comprise one or more of ranibizumab (brand name Lucentis®); aflibercept (brand name Eylea®); bevacizumab (brand name Avastin®) and OPT-302.

The double-barrelled syringe according to any one of the above aspects may allow contents of a first barrel and a second barrel to be injected simultaneously or substantially simultaneously.

The volume of the pharmaceutical composition comprised in the syringe according to any one of the above aspects may be 0.05 to 0.15 ml. The volume may comprise 0.05, 0.06, 0.07, 0.08, 0.09, 0.10, 0.11, 0.12, 0.13, 0.14 or 0.15 ml. In a particular embodiment, the volume comprises 0.1 ml.

In another embodiment of any one of the above aspects the syringe comprises a needle comprising a length of 8 to 15 mm. The length may comprise 8, 9, 10, 11, 12, 13, 14 or 15 mm. In a particular embodiment the length comprises 12 mm.

In a preferred embodiment of any one of the above aspects the syringe is prefixed with a needle.

The syringe according to any one of the above aspects may comprise one or more polymer or glass. In a particular embodiment the syringe comprises glass.

In another embodiment of any one of aspects three to eight, the pharmaceutical composition may further comprise 0.6 to 0.7 carboxy methyl cellulose (CMC). The pharmaceutical composition may comprise 0.61, 0.62, 0.63, 0.64, 0.65, 0.66, 0.67, 0.68, 0.69, 0.70, 0.71, 0.72, 0.73, 0.74 or 0.75% of carboxy methyl cellulose (CMC).

In still another embodiment of any one of aspects three to eight, the pharmaceutical composition may comprise 0.02 to 0.035 of a surfactant. The pharmaceutical composition may comprise 0.02, 0.021, 0.022, 0.023, 0.024, 0.025, 0.026, 0.027, 0.028, 0.029, 0.030, 0.031, 0.032, 0.033, 0.034, 0.35, 0.036, 0.037, 0.038, 0.039 or 0.04 of a surfactant.

The surfactant according to any one of the above aspects may comprise a polysorbate. The polysorbate may comprise one or more of polysorbate 20 and polysorbate 80. In a particular embodiment the surfactant comprises polysorbate 80.

In one embodiment of any one of the above aspects, the one or more glucocorticoid or mineralocorticoid or a therapeutically active analogue, derivative, homolog, pharmaceutically acceptable salt or conjugate thereof is comprised in at least two particle sizes. The at least two particle sizes may comprise a smaller particle size and a larger particle size. The smaller particle size may comprise less than 10 µm. The larger particle size may comprise 10 to 40 µm. The larger particle size may comprise a mean of 25 µm.

When the at least two particle sizes comprises two particle sizes, the ratio may comprise 9:1; 7:1; 6:1; 5:1; 4:1; 3:1; 2:1 or 1:1.

In one embodiment of any one of the above aspects, the pharmaceutical composition further comprises one or more of a pH adjustment composition and water for injection. The pH adjustment composition may comprise hydrochloric acid and/or sodium hydroxide.

In another embodiment of any one of the above aspects the pharmaceutical composition comprises a pH from 6 to 8. The pH may comprise from 6 to 7.5.

In still another embodiment of any one of the above aspects the pharmaceutical composition comprises a viscosity of 2 to 15 cps. The viscosity may comprise 2, 3, 4, 5, 6, 7, 8, 9, 10, 11, 12, 13, 14 o5 15 cps.

In yet another embodiment of any one of the above aspects the pharmaceutical composition may comprise a degree of flocculation of about 9.5 or greater.

In one embodiment of any one of the above aspects, the pharmaceutical composition or sterile, liquid carrier suitable for direct injection into an eye comprises a balanced salt solution. The balanced salt solution may comprise a saline and a buffer. The balanced salt solution may comprise one or more of sodium chloride; potassium chloride; calcium chloride (dehydrate); magnesium chloride (hexahydrate); sodium acetate (trihydrate); sodium citrate (dehydrate); hydrochloric acid; sodium hydroxide and water for injection.

In another embodiment of any one of the above aspects, the pharmaceutical composition or the sterile, liquid carrier suitable for direct injection into an eye comprises a hemp seed oil. The hemp seed oil may comprise sterile, cold pressed hemp seed oil.

In another embodiment of any one of the above aspects, the one or more glucocorticoid or mineralocorticoid or a therapeutically active analogue, derivative, homolog, pharmaceutically acceptable salt or conjugate thereof comprises a mixture of one or more glucocorticoid or a therapeutically active analogue, derivative, homolog, pharmaceutically acceptable salt or conjugate thereof and one or more mineralocorticoid or a therapeutically active analogue, derivative, homolog, pharmaceutically acceptable salt or conjugate thereof. The mixture may comprise: two or more glucocorticoids; one or more mineralocorticoid and one or more glucocorticoids; or two or more mineralocorticoids.

In another embodiment of any one of the above aspects, the pharmaceutical composition may comprise 2.0 to 8.0 mg of the one or more glucocorticoid or mineralocorticoid or a therapeutically active analogue, derivative, homolog, pharmaceutically acceptable salt or conjugate thereof. The pharmaceutical composition may comprise 0.4; 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0 mg of the one or more glucocorticoid or mineralocorticoid or a therapeutically active analogue, derivative, homolog, pharmaceutically acceptable salt or conjugate thereof. In particular embodiments, the pharmaceutical composition comprises 400 µg; 1.0 mg; 2.0 mg; or 4.0 mg of the one or more glucocorticoid or mineralocorticoid or a therapeutically active analogue, derivative, homolog, pharmaceutically acceptable salt or conjugate thereof.

In still another particular embodiment of any one of the above aspects, the concentration of the one or more glucocorticoid or mineralocorticoid or a therapeutically active analogue, derivative, homolog, pharmaceutically acceptable salt or conjugate thereof may be 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 mg/ml. In a particular embodiment, the concentration comprises 40 mg/ml.

In a particular embodiment of any one of the above aspects, the one or more glucocorticoid or mineralocorticoid or a therapeutically active analogue, derivative, homolog, pharmaceutically acceptable salt or conjugate thereof may comprise 0.1 ml of a 40 mg/ml solution.

In other particular embodiments of any one of the above aspects, the concentration of the one or more glucocorticoid or mineralocorticoid or a therapeutically active analogue, derivative, homolog, pharmaceutically acceptable salt or conjugate thereof may be 400 µg/0.1 mL; 1 mg/0.1 mL; or 2 mg/0.1 mL.

In another particular embodiment of any one of the above aspects, the pharmaceutical composition is preservative free.

According to any one of the above aspects, the glucocorticoid may comprise one or more of: cortisol, cortisone, prednisone, prednisolone, methylprednisolone, dexamethasone, betamethasone, triamcinolone, triamcinolone acetonide, beclometasone or a therapeutically active analogue, derivative, homolog, pharmaceutically acceptable salt or conjugate thereof.

The mineralocorticoid according to any one of the above aspects, the glucocorticoid or mineralocorticoid or a therapeutically active analogue, derivative, homolog, pharmaceutically acceptable salt or conjugate thereof may comprise one or more of: 11-desoxycortisone (11-DC); fludrocortisone; fludrocortisone acetate (FA); Deoxycorticosterone acetate (DA); Deoxycorticosterone (DS); or Aldosterone; or a therapeutically active analogue, derivative, homolog, pharmaceutically acceptable salt or conjugate thereof.

The one or more glucocorticoid or mineralocorticoid or a therapeutically active analogue, derivative, homolog, pharmaceutically acceptable salt or conjugate thereof according to any one of the above aspects may comprise one or more dual action compounds, wherein each dual action compound is capable of modulating the activity of both a mineralocorticoid receptor and a glucocorticoid receptor.

According to any of the above aspects, the dual action compound may comprise one or more of triamcinolone acetonide; cortisol; cortisone; prednisone; prednisolone; methylprednisolone; fludrocortisone; fludrocortisone acetate or a therapeutically active analogue, derivative, homolog, pharmaceutically acceptable salt or conjugate thereof.

In one particular embodiment of any one of the above aspects, the one or more glucocorticoid or mineralocorticoid or a therapeutically active analogue, derivative, homolog, pharmaceutically acceptable salt or conjugate thereof comprises triamcinolone acetonide or a therapeutically active analogue, derivative, homolog, pharmaceutically acceptable salt or conjugate thereof. When the one or more glucocorticoid or mineralocorticoid or a therapeutically active analogue, derivative, homolog, pharmaceutically acceptable salt or conjugate thereof comprises triamcinolone acetonide the concentration may comprise 3.0 to 5.0 mg/ml. In one particular embodiment the concentration may comprise 4.0 mg/ml.

In another particular embodiment of any one of the above aspects, the one or more glucocorticoid or mineralocorticoid or a therapeutically active analogue, derivative, homolog, pharmaceutically acceptable salt or conjugate thereof comprises fludrocortisone acetate or a therapeutically active analogue, derivative, homolog, pharmaceutically acceptable salt or conjugate thereof.

In another particular embodiment of any one of the above aspects, the one or more glucocorticoid or mineralocorticoid or a therapeutically active analogue, derivative, homolog, pharmaceutically acceptable salt or conjugate thereof comprises triamcinolone acetonide and fludrocortisone acetate or a therapeutically active analogue, derivative, homolog, pharmaceutically acceptable salt or conjugate of either or both.

In another particular embodiment of any one of the above aspects, the one or more glucocorticoid or mineralocorticoid or a therapeutically active analogue, derivative, homolog, pharmaceutically acceptable salt or conjugate thereof comprises triamcinolone acetonide and fludrocortisone acetate or a therapeutically active analogue, derivative, homolog, pharmaceutically acceptable salt or conjugate of either or both.

In yet another particular embodiment of any one of the above aspects, the pharmaceutical composition may comprise a powder. The powder may comprise a dry powder and/or may lack any delivery vehicle.

According to any one of the above aspects, said eye disease and/or condition or predisposition thereto may be an exudative eye disease and/or condition.

According to any one of the above aspects, said eye disease and/or condition or predisposition thereto may be a back of the eye exudative eye disease and/or condition.

According to any one of the above aspects, said eye disease and/or condition or predisposition thereto may be a front of the eye exudative eye disease and/or condition.

According to any one of the above aspects, said eye disease and/or condition or predisposition thereto may be macular degeneration including age-related macular degeneration and wet age related macular degeneration.

According to any one of the above aspects, said eye disease and/or condition or predisposition thereto may be a diabetic macular edema (DME), cystoid macular edema (CMO); maculopathy; and/or an ocular tumour.

The ocular tumour may comprise a retinoblastoma and/or a melanoma.

According to any one of the above aspects, said eye disease and/or condition or predisposition thereto may be a diabetic eye disease and/or condition.

Other eye disease and/conditions include (non-infectious) conjunctivitis, anterior uveitis and an ocular allergy.

According to any of the above aspects, the eye disease and/or condition or predisposition thereto may comprise one or more of macular degeneration, maculopathy including an age related maculopathy (ARM), age related macular degeneration (AMD) including both the dry (geographic atrophy) and wet (choroidal neovascularisation (CNV)), an exudative eye disease or condition, retinal pigment epithelium detachments (PED), forms of age related macular degeneration, a diabetic eye disease or condition including a diabetic retinopathy and diabetic macular edema (DME), corneal neovascularisation, cyclitis, Hippel-Lindel disease, retinopathy of prematurity (also known as retrolental fibroplasia), pterygium, histoplasmosis, iris neovascularisation, glaucoma, glaucoma-associated neovascularisation, Purtcher's retinopathy, ocular hypertension, macular edema, Coats' disease, uveitis including anterior uveitis, Sicca syndrome, hereditary diseases associated with increased extra-intracellular lipid storage/accumulation, juvenile macular degeneration, an ocular allergy, oedema secondary to vein occlusion and an ocular tumour.

According to any one of the above aspects, the eye disease and/or condition or predisposition thereto may comprise a back of eye disease or conditions including an exudative back of eye exudative disease or condition. The back of eye disease or condition may comprise an eye disease or condition involving the retina, macular and/or fovea in the posterior region of the eye. Examples of back of eye disease include macular oedema, such as clinical macular oedema or angiographic cystoid macular oedema arising from various aetiologies, such as diabetes, exudative macular degeneration and macula oedema arising from laser treatment of the retina, retinal ischemia and choroidal neovascularisation, a retinal disease, an inflammatory disease, uveitis associated with neoplasms, such as retinoblastoma or psuedoglioma, neovascularisation following vitrectomy, a vascular disease and neovascularisation of the optic nerve.

The retinal disease may be one or more of diabetic retinopathy, diabetic retinal oedema, retinal detachment, senile macular degeneration due to sub-retinal neovascularisation and myopic retinopathy.

The vascular disease may be one or more of retinal ischemia, choroidal vascular insufficiency, choroidal thrombosis and neovascular retinopathies resulting from carotoid artery ischemia.

According to any one of the above aspects, the eye disease and/or condition or predisposition thereto may also comprise a front of eye disease or condition which predominantly involves the tissue at the front of the eye, such as the cornea, iris, ciliary body and conjunctiva including an exudative front of eye disease or condition. The front of eye disease may be one or more of corneal neovascularisation, a corneal disease or opacification with an exudative or inflammatory component, diffuse lamellar keratitis, neovascularisation due to penetration of the eye or contusive ocular injury, rubosis iritis, Fuchs' heterochromic iridocyclitis, chronic uveitis, anterior uveitis, inflammatory conditions resulting from surgeries such as LASIK, LASEK, refractive surgery, IOL implantation; irreversible corneal oedema as a complication of cataract surgery, oedema as a result of insult or trauma, inflammation, infectious and non-infectious conjunctivitis, keratoconjunctivitis, iridocyclitis, iritis, scleritis, episcleritis, infectious keratitis, superficial punctuate keratitis, keratoconus, posterior polymorphous dystrophy, Fuch's dystrophies, aphakic and pseudophakic bullous keratopathy, corneal oedema, scleral disease, ocular cicatrcial pemphigoid, pars planitis, Posner Schlossman syndrome, Behcet's disease, Vogt-Koyanagi-Harada syndrome, hypersensitivity reactions, ocular surface disorders, conjunctival oedema, Toxoplasmosis chorioretinitis, inflammatory pseudotumor of the orbit, chemosis, conjunctival venous congestion, periorbiatal cellulits, acute dacroycystitis, non-specific vasculitis, sarcoidosis and cytomegalovirus infection.

The invention according to any above aspect may further comprise one or more pharmaceutically acceptable carriers, diluents or excipients.

The one or more pharmaceutically acceptable carriers, diluents or excipients may comprise one or more surfactants or wetting agent.

According to any one of the above aspects, the compositions of the invention may comprise a sustained release composition.

In a particular embodiment of any one of the above aspects, the pharmaceutical compositions may be sterilized.

In another particular embodiment of any one of the above aspects, a unit dose comprises the pharmaceutical composition in the form in which it is to be used. The unit dose may comprise the pharmaceutical composition in a particular dose; volume; particle size; pH; viscosity; and/or degree of flocculation. The unit dose may comprise non-reusable packaging. The non-reusable packaging may comprise the syringe or double-barrelled syringe. The provision of a unit dose may decrease error and/or increase ease of use.

According to any one of the above aspects, the composition may comprise a sufficient injectability to be injected into an eye.

As used herein, except where the context requires otherwise, the term "comprise" and variations of the term, such as "comprising", "comprises" and "comprised", are not intended to exclude further additives, components, integers or steps.

BRIEF DESCRIPTION OF THE FIGURES

In order that the present invention may be readily understood and put into practical effect, reference will now be made to the accompanying illustrations, wherein like reference numerals refer to like features and wherein.

DETAILED DESCRIPTION OF THE INVENTION

Figure 1:
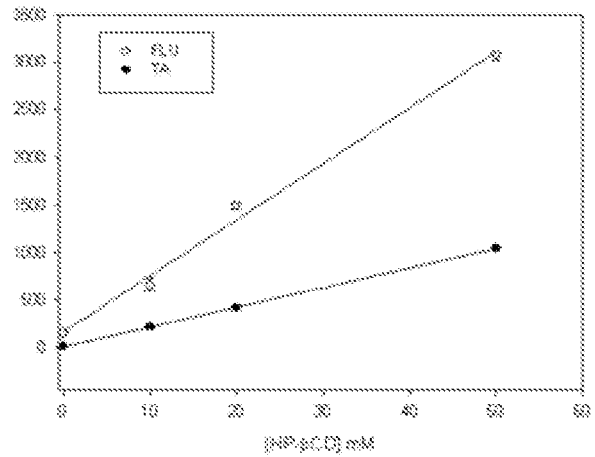
FIG. 1: Solubility enhancement for MR compounds and TA in saline with addition of hydroxy propyl β-cyclodextrin (data are mean±sd, n=3). Top: FLU and TA; Bottom: 11-DC; DCS and DCSA.
Figure 1:
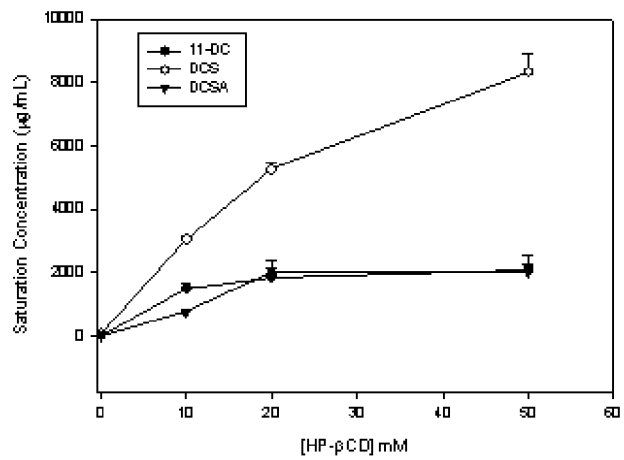

The invention relates to a medical device, pharmaceutical composition and method for making a pharmaceutical composition for treating an eye disease or condition including a diabetic eye disease and an ocular tumour.

The invention is at least partly predicated on the unexpected discovery that a prefilled syringe comprising a unit dose pharmaceutical composition has significant advantages. These advantages include improved ease of use for the health care professional administering the injection and greater cost-effectiveness compared to multi-dose vials. Multi-dose vials can result in a large amount of waste when regulatory regimes only permit one use of a vial. Additionally, the tailored, single unit dose provided by the present invention is safer, more cost effective and more accurate than the multi-dose formulations.

As used herein, the term "unit dose" is used to refer to a pharmaceutical composition in the form in which it is to be used. The unit dose may comprise the pharmaceutical composition of the invention in a particular dose; volume; particle size; pH; viscosity; and/or degree of flocculation. The unit dose may comprise the non-reusable packaging such as, the syringe or double-barrelled syringe.

The present invention facilitates adjunct usage of steroids with other ocular therapies. Advantageously, this minimises the number of injections requires by increasing the efficacy and safety of the procedure. In some embodiments, the present invention provides a steroidal medicament in combination with one or more other ocular therapeutic, which advantageously exposes the target tissue to both drugs accurately and simultaneously.

In one embodiment, the unit dose formulation provided by the present inventors, is furnished in a 27 gauge needle that has a thinner body for good grip. The improved grip provided by the present claimed invention makes injection easier and reduces any risk of injection error. The 27 gauge needle may comprise a 27 G thin wall needle.

In one form the invention relates to a unit dose pharmaceutical composition comprising 2.0 to 8.0 mg of one or more glucocorticoid or mineralocorticoid or a therapeutically active analogue, derivative, homolog, pharmaceutically acceptable salt or conjugate thereof.

The unit dose pharmaceutical formulation may comprise 2.0 to 8.0 mg of one or more glucocorticoid or mineralocorticoid or a therapeutically active analogue, derivative, homolog, pharmaceutically acceptable salt or conjugate thereof in a dry powder form wherein the unit dose pharmaceutical composition is comprised in a syringe.

In another form the invention relates to a medical device comprising the unit dose pharmaceutical composition, the composition comprising 2.0 to 8.0 mg of a dry powder of one or more glucocorticoid or mineralocorticoid or a therapeutically active analogue, derivative, homolog, pharmaceutically acceptable salt or conjugate thereof; wherein the unit dose pharmaceutical composition is comprised in a syringe. With the composition comprised in a syringe, the medical device may be comprised of a syringe.

The provision of the composition or medicament as a dry powder gives the clinician of choice of vehicle. The dry powder format is of great advantage, because this dry powder presentation allows long term storage and stability. Once put with its vehicle, the one or more glucocorticoid or mineralocorticoid or a therapeutically active analogue, derivative, homolog, pharmaceutically acceptable salt or conjugate thereof starts to degrade. The dry powder format preserves potency and allows long term storage so that the same potency is available at the beginning and end of a year study. This also has an advantage in terms of ease of sterilisation and in terms of shipping, shelf life and longevity.

In some embodiments, the dry powder may be suspended in a vehicle of choice such as, a sterile, liquid carrier suitable for direct injection into an eye.

In one embodiment, the unit dose pharmaceutical composition and medical device may also comprise 0.6 to 0.75% (w/v) of CMC. In another embodiment, the unit dose pharmaceutical composition comprises 0.6 to 0.7 (w/v) CMC. The pharmaceutical composition may comprise 0.61, 0.62, 0.63, 0.64, 0.65, 0.66, 0.67, 0.68, 0.69, 0.70, 0.71, 0.72, 0.73, 0.74 or 0.75% (w/v) of CMC.

In one embodiment, the unit dose pharmaceutical composition and medical device may comprise 0.015 to 0.04% (w/v) of a surfactant. In another embodiment, the surfactant is comprises at 0.02 to 0.035% (w/v). The pharmaceutical composition may comprise 0.02, 0.021, 0.022, 0.023, 0.024, 0.025, 0.026, 0.027, 0.028, 0.029, 0.030, 0.031, 0.032, 0.033, 0.034, 0.35, 0.036, 0.037, 0.038, 0.039 or 0.04 (w/v) of the surfactant.

As used herein, the term "surfactant" refers to any agent, which preferentially absorbs to an interface between two immiscible phases, such as the interface between water and an organic polymer solution, a water/air interface or organic solvent/air interface. Surfactants generally possess a hydrophilic moiety and a lipophilic moiety; such that, upon absorbing to microparticles, they tend to present moieties to the external environment that do not attract similarly coated particles, thus reducing particle agglomeration. Surfactants may also promote absorption of a therapeutic or diagnostic agent and increase bioavailability of the agent.

The surfactant may comprise a polysorbate, such as one or more of polysorbate 20 and polysorbate 80. In a preferred embodiment, the surfactant comprises polysorbate 80.

One of the particular advantages of the present invention is that the unit dose pharmaceutical composition may be comprised in a syringe.

According to the present invention the unit dose pharmaceutical composition may be used in the treatment of an eye disease or condition or predisposition thereto.

Also provided is a method of treatment of an eye disease or condition or a predisposition thereto in a subject in need thereof, the method including injecting into the eye the unit dose pharmaceutical formulation. The injection may comprise intravitreal and/or suprachoroidal injection.

The unit dose pharmaceutical composition of the invention may also find use in the manufacture of a medicament for the therapeutic and/or prophylactic treatment of an eye disease or condition.

The invention also provides a syringe comprising the unit dose pharmaceutical composition.

The syringe may comprise a 25 to 30 gauge. The gauge may comprise 25, 26, 27, 28, 29 or 30 gauge. In a particular embodiment the gauge comprises 27.

The syringe may comprise a volume of 0.25 to 0.75 ml. The volume may comprise 0.25, 0.30, 0.35, 0.40, 0.45, 0.50, 0.55, 0.60, 0.65, 0.70 or 0.75 ml. In a preferred embodiment volume comprises 0.50 ml.

The volume of the pharmaceutical composition comprised in the syringe may be 0.05 to 0.15 ml. The volume may comprise 0.05, 0.06, 0.07, 0.08, 0.09, 0.10, 0.11, 0.12, 0.13, 0.14 or 0.15 ml. In a particular embodiment, the volume comprises 0.1 ml.

The syringe may be a double-barrelled syringe. Each barrel may have the dimensions listed above. The first barrel may comprise a pharmaceutical composition of the invention and the second barrel may comprise another medicament. The another medicament may comprise an anti-VEGF. The anti-VEGF may comprise one or more of ranibizumab (brand name Lucentis®); aflibercept (brand name Eylea®); bevacizumab (brand name Avastin®) and OPT-302 available from Opthea (www.opthea.com).

The needle comprised on the syringe may comprise a length of 8 to 15 mm. The length may comprise 8, 9, 10, 11, 12, 13, 14 or 15 mm. In a particular embodiment the length comprises 12 mm.

The syringe may be prefixed with the needle. The needle may be removable or permanently attached. In a particular embodiment, the needle is permanently attached and the syringe is disposable.

The syringe may comprise one or more polymer or glass. In a particular embodiment the syringe comprises glass.

The one or more glucocorticoid or mineralocorticoid or a therapeutically active analogue, derivative, homolog, pharmaceutically acceptable salt or conjugate thereof may be comprised in at least two particle sizes. The at least two particle sizes may comprise a smaller particle size and a larger particle size. The smaller particle size may comprise less than 10 µm. The larger particle size may comprise 10 to 40 µm. The larger particle size may comprise a mean of 25 µm.

When the at least two particle sizes comprises two particle sizes, the ratio may comprise 9:1; 7:1; 6:1; 5:1; 4:1; 3:1; 2:1 or 1:1.

The pharmaceutical composition may further comprise one or more of a pH adjustment composition and water for injection. The pH adjustment composition may comprise hydrochloric acid and/or sodium hydroxide.

The pharmaceutical composition may comprise a pH from 6 to 8. The pH may comprise from 6 to 7.5.

The pharmaceutical composition may comprise a viscosity of 2 to 15 cps. The viscosity may comprise 2, 3, 4, 5, 6, 7, 8, 9, 10, 11, 12, 13, 14 or 15 cps.

The pharmaceutical composition may comprise a degree of flocculation of about 9.5 or greater.

The pharmaceutical composition may comprise a balanced salt solution. The balanced salt solution may comprise a saline and a buffer. The balanced salt solution may comprise may comprise one or more of sodium chloride; potassium chloride; calcium chloride (dehydrate); magnesium chloride (hexahydrate); sodium acetate (trihydrate); sodium citrate (dehydrate); hydrochloric acid; sodium hydroxide and water for injection.

The pharmaceutical composition or the sterile, liquid carrier suitable for direct injection into an eye may comprise a hemp seed oil such as, sterile, cold pressed hemp seed oil.

The one or more glucocorticoid or mineralocorticoid or a therapeutically active analogue, derivative, homolog, pharmaceutically acceptable salt or conjugate thereof comprises a mixture of one or more glucocorticoid and one or more mineralocorticoid a therapeutically active analogue, derivative, homolog, pharmaceutically acceptable salt or conjugate thereof. The mixture may comprise: two or more glucocorticoids; one or more mineralocorticoid and one or more glucocorticoids; or two or more mineralocorticoids.

In a particular embodiment, the one or more glucocorticoid or mineralocorticoid or a therapeutically active analogue, derivative, homolog, pharmaceutically acceptable salt or conjugate thereof comprises triamcinolone acetonide or a therapeutically active analogue, derivative, homolog, pharmaceutically acceptable salt or conjugate thereof. When the one or more glucocorticoid or mineralocorticoid or a therapeutically active analogue, derivative, homolog, pharmaceutically acceptable salt or conjugate thereof comprises triamcinolone acetonide the concentration may comprise 3.0 to 5.0 mg/ml. In one particular embodiment the concentration may comprise 4.0 mg/ml.

The pharmaceutical composition may comprise 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0 mg of the one or more glucocorticoid or mineralocorticoid or a therapeutically active analogue, derivative, homolog, pharmaceutically acceptable salt or conjugate thereof. In a particular embodiment, the pharmaceutical composition comprises 400 µg; 1.0 mg; 2.0 mg or 4.0 mg of the one or more glucocorticoid or mineralocorticoid a therapeutically active analogue, derivative, homolog, pharmaceutically acceptable salt or conjugate thereof.

The concentration of the one or more glucocorticoid or mineralocorticoid or a therapeutically active analogue, derivative, homolog, pharmaceutically acceptable salt or conjugate thereof may be may be 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 mg/ml. In a particular embodiment, the concentration comprises 40 mg/ml.

The one or more glucocorticoid or mineralocorticoid or a therapeutically active analogue, derivative, homolog, pharmaceutically acceptable salt or conjugate thereof may comprise 0.1 ml of a 40 mg/ml solution.

The unit dose formulation may comprise 4.0 mg of triamcinolone acetonide.

In a particular embodiment of any above aspect, the pharmaceutical composition is preservative free.

The one or more glucocorticoid or a therapeutically active analogue, derivative, homolog, pharmaceutically acceptable salt or conjugate thereof may comprise one or more of: cortisol, cortisone, prednisone, prednisolone, methylprednisolone, dexamethasone, betamethasone, triamcinolone, triamcinolone acetonide, beclometasone or a therapeutically active analogue, derivative, homolog, pharmaceutically acceptable salt or conjugate thereof.

The one or more mineralocorticoid may comprise one or more of: 11-desoxycortisone (11-DC); fludrocortisone; fludrocortisone acetate (FA); Deoxycorticosterone acetate (DA); Deoxycorticosterone (DS); or Aldosterone; or a therapeutically active analogue, derivative, homolog, pharmaceutically acceptable salt or conjugate thereof.

The one or more glucocorticoid or mineralocorticoid or a therapeutically active analogue, derivative, homolog, pharmaceutically acceptable salt or conjugate thereof may comprise one or more dual action compounds, wherein each dual action compound is capable of modulating the activity of both a mineralocorticoid receptor and a glucocorticoid receptor.

The dual action compound may comprise one or more of triamcinolone acetonide (TA); cortisol; cortisone; prednisone; prednisolone; methylprednisolone; fludrocortisone acetate or a therapeutically active analogue, derivative, homolog, pharmaceutically acceptable salt or conjugate thereof.

In another particular embodiment of any of the above aspects, the one or more glucocorticoid or mineralocorticoid or a therapeutically active analogue, derivative, homolog, pharmaceutically acceptable salt or conjugate thereof comprises fludrocortisone acetate or a therapeutically active analogue, derivative, homolog, pharmaceutically acceptable salt or conjugate thereof.

Fludrocortisone acetate (9-α-Fiuoro-11β. 17α, 21-trihydroxy-4-pregnene-3, 20 dione acetate) (FCA) is a synthetic steroid possessing a potent mineralocorticoid effect and a high glucocorticoid activity. FCA is a synthetic corticosteroid with anti-inflammatory and anti-allergic properties. FCA is a mineralocorticoid receptor and glucocorticoid receptor agonist that binds to cytoplasmic receptors, translocates to the nucleus and subsequently initiates the transcription of glucocorticoid-responsive genes such as lipocortins to inhibit phospholipase A2. This prevents the release of arachidonic acid, a precursor to prostaglandins and leukotrienes, both important mediators in the pro-inflammatory response mechanism. In addition, this agent exerts its mineralocorticoid effect on the distal tubules and collecting ducts of the kidney by inducing permease, an enzyme that regulates Na+ permeability in cells, thereby enhancing Na+ reabsorption and water retention as well as increasing $K^+$, $H^+$ excretion In another particular embodiment of any of the above aspects, the one or more glucocorticoid or mineralocorticoid or a therapeutically active analogue, derivative, homolog, pharmaceutically acceptable salt or conjugate thereof comprises triamcinolone acetonide and fludrocortisone acetate or a therapeutically active analogue, derivative, homolog, pharmaceutically acceptable salt or conjugate of either.

The pharmaceutical composition may comprise a powder. The powdered form of the pharmaceutical composition lacks any delivery vehicle, i.e. no liquid is provided with the powdered form. The powdered form may be injected as is done with the pharmaceutical composition provided with a liquid delivery vehicle. Alternatively, a liquid delivery vehicle may be added prior to injection. The powdered form may advantageously have an extended shelf life.

As used herein, the term "eye condition" includes any eye condition such as, early or sub-clinical stages of an eye disease.

As used herein, the term "eye disease" includes any eye disease such as, macular degeneration, maculopathy including an age related maculopathy (ARM), age related macular degeneration (AMD) including both the dry (geographic atrophy) and wet (choroidal neovascularisation (CNV)), an exudative eye disease or condition, retinal pigment epithelium detachments (PED), forms of age related macular degeneration, a diabetic eye disease or condition including a diabetic retinopathy and diabetic macular edema (DME), corneal neovascularisation, cyclitis, Hippel-Lindel disease, retinopathy of prematurity (also known as retrolental fibroplasia), pterygium, histoplasmosis, iris neovascularisation, glaucoma, glaucoma-associated neovascularisation, Purtcher's retinopathy, ocular hypertension, macular edema, Coats' disease, uveitis including anterior uveitis, Sicca syndrome, hereditary diseases associated with increased extra-intracellular lipid storage/accumulation, juvenile macular degeneration, an ocular allergy, oedema secondary to vein occlusion and an ocular tumour. The ocular tumour may comprise a retinoblastoma and/or a melanoma.

The eye disease or condition may comprise a back of eye disease or conditions including an exudative back of eye exudative disease or condition. The back of eye disease or condition may comprise an eye disease or condition involving the retina, macular and/or fovea in the posterior region of the eye. Examples of back of eye disease include macular oedema, such as clinical macular oedema or angiographic cystoid macular oedema arising from various aetiologies, such as diabetes, exudative macular degeneration and macula oedema arising from laser treatment of the retina, retinal ischemia and choroidal neovascularisation, a retinal disease, an inflammatory disease, uveitis associated with neoplasms, such as retinoblastoma or psuedoglioma, neovascularisation following vitrectomy, a vascular disease and neovascularisation of the optic nerve. The retinal disease may be one or more of diabetic retinopathy, diabetic retinal oedema, retinal detachment, senile macular degeneration due to sub-retinal neovascularisation and myopic retinopathy. The vascular disease may be one or more of retinal ischemia, choroidal vascular insufficiency, choroidal thrombosis and neovascular retinopathies resulting from carotid artery ischemia.

The eye disease or condition may also comprise a front of eye disease or condition which predominantly involves the tissue at the front of the eye, such as the cornea, iris, ciliary body and conjunctiva including an exudative front of eye disease or condition. The front of eye disease may be one or more of corneal neovascularisation, a corneal disease or opacification with an exudative or inflammatory component, diffuse lamellar keratitis, neovascularisation due to penetration of the eye or contusive ocular injury, rubosis iritis, Fuchs' heterochromic iridocyclitis, chronic uveitis, anterior uveitis, inflammatory conditions resulting from surgeries such as LASIK, LASEK, refractive surgery, IOL implantation; irreversible corneal oedema as a complication of cataract surgery, oedema as a result of insult or trauma, inflammation, infectious and non-infectious conjunctivitis, keratoconjunctivitis, iridocyclitis, iritis, scleritis, episcleritis, infectious keratitis, superficial punctuate keratitis, keratoconus, posterior polymorphous dystrophy, Fuch's dystrophies, aphakic and pseudophakic bullous keratopathy, corneal oedema, scleral disease, ocular cicatrcial pemphigoid, pars planitis, Posner Schlossman syndrome, Behcet's disease, Vogt-Koyanagi-Harada syndrome, hypersensitivity reactions, ocular surface disorders, conjunctival oedema, Toxoplasmosis chorioretinitis, inflammatory pseudotumor of the orbit, chemosis, conjunctival venous congestion, periorbiatal cellulits, acute dacroycystitis, non-specific vasculitis, sarcoidosis and cytomegalovirus infection.

The pharmaceutical compositions of the invention may have atherapeutic effect with regards to oedema, swelling and/or neovascularisation in the tumor. Glucocorticoids and mineralocorticoids are also known to reduce inflammation and to help relieve nausea when having chemotherapy.

The invention may find application to an exudative eye disease and/or condition, a back of the eye exudative eye disease and/or condition, a front of the eye exudative eye disease and/or condition, age-related macular degeneration, wet age related macular degeneration, a diabetic macular edema (DME), cystoid macular edema (CMO); maculopathy; and/or an ocular tumour. The ocular tumour may comprise a retinoblastoma and/or a melanoma. The eye disease and/or condition may be a diabetic eye disease and/or condition. Other eye disease and/conditions include (non-infectious) conjunctivitis, anterior uveitis and an ocular allergy.

"Prevention" or "prophylaxis," as used herein, refers to prophylactic or preventative measures. Those in need of prevention or prophylaxis include those in whom the eye disease or condition is to be prevented, and in some embodiments, may be predisposed or susceptible to the eye disease or condition e.g. individuals with a family history of an eye disease or condition.

Prevention or prophylaxis is successful herein if the development of an eye disease or condition is completely or partially prevented or slowed down.

"Treatment" of a subject herein refers to therapeutic treatment. Those in need of treatment include those already with an eye disease or condition, as well as those in whom the progress of an eye disease or condition is to be prevented. Hence, the subject may have been diagnosed as having the eye disease or condition or may have an eye disease or condition or damage that is likely to progress in the absence of treatment. Alternatively, the subject may be symptom-free, but has risk factors for development of an eye disease or condition e.g., positive family history. Treatment is successful herein if the eye disease or condition is alleviated or healed, or progression of the eye disease or condition, including its signs and symptoms and/or structural damage, is halted or slowed down as compared to the condition of the subject prior to administration. Successful treatment further includes complete or partial prevention of the development of the eye disease or condition. For purposes herein, slowing down or reducing the eye disease or condition or the progression of the eye disease or condition is the same as arrest, decrease, or reversal of the eye disease or condition.

The expression "effective amount" refers to an amount of an agent or medicament, either in a single dose or as part of a series, which is effective for treating or preventing an eye disease or condition or predisposition thereto. This would include an amount that is effective in achieving a reduction in one or more symptom as compared to baseline prior to administration of such amount as determined, e.g., by visual acuity or other testing. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The terms "subject", "patient" or "individual," which are used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including humans, as well as non-human primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. In specific embodiments, the "subject", "patient" or "individual" is a human in need of treatment or prophylaxis of an eye disease or condition, including in subjects with a diabetic eye disease or condition or an ocular tumour. In specific embodiments, the terms "subject", "patient" or "individual" refer to any single human subject, including a patient, eligible for treatment who is experiencing or has experienced one or more signs, symptoms, or other indicators of an eye disease or condition or predisposition thereto, whether, for example, newly diagnosed or previously diagnosed and now experiencing a recurrence or relapse, or is at risk for an eye disease or condition, no matter the cause. Intended to be included as a "subject", "patient" or "individual" are any subjects involved in clinical research trials not showing any clinical sign of disease, or subjects involved in epidemiological studies, or subjects once used as controls. The "subject" "patient" or "individual" may have been previously treated with a medicament for an eye disease or condition, or not so treated.

The invention according to any above aspect may further comprise one or more pharmaceutically acceptable carriers, diluents or excipients.

In a particular embodiment of any one of the above aspects, the compound and compositions may be sterilized.

As used herein, glucocorticoid and mineralocorticoid includes a therapeutically active analog, derivative, pharmaceutically acceptable salt, prodrug, metabolite or conjugate thereof.

As used herein, a derivative includes a therapeutically active or pharmaceutically active fragment of a compound modulating the activity of a mineralocorticoid receptor or a glucocorticoid receptor.

An analog may be a structural analog or a functional analog.

A homolog may comprise a molecule of the same chemical type, but differing by a fixed increment of an atom or a constant group of atoms. An example is methyl and ethyl alcohols which are homologous.

Table 1 below shows some example compounds and their measured mineralocorticoid and glucocorticoid potencies.

In one embodiment, the compositions of the invention comprise a sustained release composition. Based on the teachings herein, a skilled person is readily able to select and/or formulate a suitable sustained release composition.

In another embodiment, the compounds and compositions may be sterilised. From the teachings herein, a skilled person is readily able to select a suitable sterilisation method such as, heat treatment.

In another embodiment, the compositions of the invention are preservative free.

In a particular embodiment, the compositions of the invention may be comprised in a syringe. In one embodiment, the syringe allows direct injection into an eye.

The inventors have also provided a pharmaceutical composition comprising the therapeutic agent described herein and optionally a pharmaceutically acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts, such as mineral acid salts including hydrochlorides, bromides and sulfates, organic acids such as acetates, propionates and malonates and pyrogen-free water.

The one or more pharmaceutically acceptable carriers, diluents or excipients may comprise one or more of a wetting agent and a viscosity modifier.

A useful reference describing pharmaceutically acceptable carriers, diluents and excipients is Remington's Pharmaceutical Sciences (Mack Publishing Co. N.J. USA, 1991), which is incorporated herein by reference.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

To allow injection, the composition may comprise a sufficient injectability to be injected into an eye. By injectability is meant that by pressing down on the plunger, the composition is injected into said eye in a controllable and consistent manner.

So that the invention may be readily understood and put into practical effect, the following non-limiting example is provided.

EXAMPLES

Unit Dose Formulation

A unit dose formulation was prepared using two commercially available triamcinolone acetonide (TA) preparations. Both preparations are available from Farmabios SpA. One preparation has a particle size less than 10 µM, the other has a particle size of 10 to 40 µM with a mean of 25 µM. The unit dose formulation comprised 0.1 ml of a 40 mg/ml solution of TA amounting to 4 mg. The final unit dose formulation also comprised 0.02 (w/v) polysorbate 80 and 0.6 (w/v) CMC. The 0.1 ml unit dose formulation was then added to a 0.5 ml, 27 gauge, glass syringe with a pre-attached 1.2 mm needle.

Squeeze Test

A squeeze test to assess the ease of use of the 27 gauge needle may be conducted.

In Vitro Release Rate/Safety or Clinical Study

Studies of the in vitro release rate, along with a safety and/or clinical study may be conducted.

Aqueous Solubility and Enhancement of Drug Solubility Using Cyclodextrin

We have investigated the solubility enhancement of hydroxy-propyl β-cyclodextrin (HP-βCD) on the solubility of the MR compounds in saline, with a view to its potential use in the suspension formulations to boost the amount of drug in solution.

FIG. 1 shows solubility enhancement for MR compounds and TA in saline with addition of hydroxy propyl β-cyclodextrin (data are mean±sd, n=3). Clearly, the solubility of FLU (fludrocortisone) and TA (triamcinolone acetonide) was enhanced >30 fold over the solubility in saline and increased linearly with cyclodextrin concentration in both cases. The absolute solubility for TA is lower overall. In an aqueous suspension formulation this would provide a much greater proportion of drug in solution at the time of administration, without the issues of reduced activity. The increases in concentration for DCS (deoxycorticosterone acetate) were close to a linear relationship, and was the greatest seen for all drugs, with the concentration in solution with 50 mM HP-βCD being >8 mg/mL. However, the concentrations for 11-DC (11-deoxycortisol) and DCSA (deoxycorticosterone acetate) plateau at around 2 mg/mL. While the reason for this is not clear, the difference between the two sets of compounds is that FLU and TA were micronised, whilst DCS, DCSA and 11-DC were not, and the 48 hr mixing time may have been insufficient to attain full saturation of drug in saline. This is also supported by the fact that DCS was closer to saturation as it has a 4-8 fold greater solubility than 11-DC and DCSA. Given longer time to equilibrate, it would be anticipated that the solubility of 11-DC and DCS A would exceed 6 mg/mL, while that of DCS may in fact reach greater than 20 mg/mL based on the slope of the curve at low cyclodextrin concentrations.

In all cases the use of hydroxypropyl hydroxy-propyl β-cyclodextrin (HP-βCD)-cyclodextrin should be considered to maximise the chance of observing a pharmacological effect with these poorly water soluble drugs.

Drug Storage Stability in Saline

To best ensure sterility of a final dose form, it was felt that a terminal sterilization approach in flame sealed glass ampoules would be the preferred approach, yielding a 'Kenalog' style product, however this would necessitate the drug being in an aqueous salt environment for extended periods of time. Consequently it was felt to be important to characterise the drug stability over time in aqueous solution as an indicator of likely issues with drug content and/or degradation products in the suspensions on storage. An accelerated stability trial was conducted in which saturated drug solutions were prepared in saline (as a model for BS S) and samples were stored at 60° C. for up to 14 days. This was felt to reflect likely degradation profiles over at least two-three months at ambient/refrigerated temperatures. Triplicate samples were removed from the oven at 1, 3, 7 and 14 days and analysed for drug content to follow loss of active, and the appearance of peaks in the spectrum. (A dedicated diode array detector is used with the HPLC for these studies as a powerful tool in identifying that compounds are produced that may not absorb at 240 nm and hence would not appear as 'peaks' in the single wavelength chromatogram).

Figure 2:
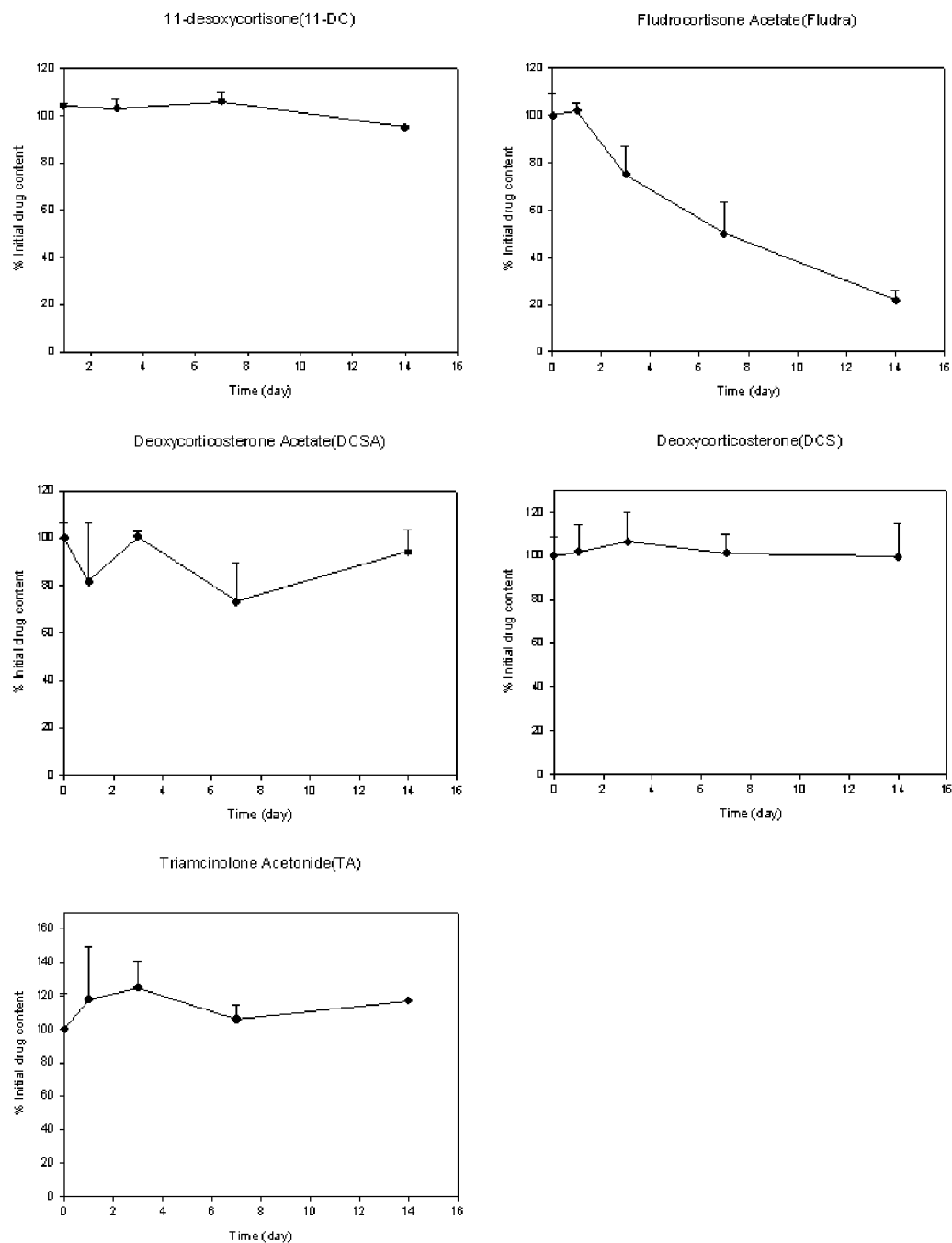
FIG. 2: Drug solubility in aqueous solution of Tween 80 over time when stored at 37° C. for 72 hr (data are mean±sd n=3 at each time point).

The profiles for drug concentration over time are presented in FIG. 2 for each drug. It is apparent that 11-DC is stable over a week, and slightly declined in the second week, but was still at a concentration >90% of that originally in the sample. Fludrocortisone displayed marked instability, declining to only 20% of the original concentration after two weeks. The remaining drugs were essentially stable over the test period. Some variability in results was evident for DCSA and TA, which we have attributed to their very low aqueous solubilities relative to the other compounds. The instability of fludrocortisone, in particular, may exclude the use of pre-packaged aqueous suspensions as a suitable dose form, at least for fludrocortisone, due to the likely production of high levels of degradation products and other avenues need to be pursued.

Drug Stability Under Sterilization Conditions (Autoclave and Gamma Irradiation)

Drug Aqueous Solutions

Preferably, the study materials are sterile, at least to a large degree for preclinical studies. In the absence of a facility for complete aseptic manufacture, in order to sterilize the suspensions there are two possible approaches foreseen—autoclaving the final suspensions in 'vial', or gamma sterilization. Consequently, in order to initially test the resistance of the drug to degradation in the 'wet' environment, drug in saturated solutions were prepared as for the storage stability studies above and subjected to autoclave conditions (121° C./30 min) or gamma irradiation (~25 kGy at ambient temperature).

Gamma irradiation was conducted at a firm in Melbourne (Steritech; 160 South Gippsland Hwy, Dandenong Sth) and QC certificates provided verifying dose of gamma irradiation received. The samples were exposed to 25 kGy radiation, which severely discoloured the vials, in long term this method may be very suitable when an appropriate glass container, resistant to gamma rays, is used for sample preparation.

Figure 3:
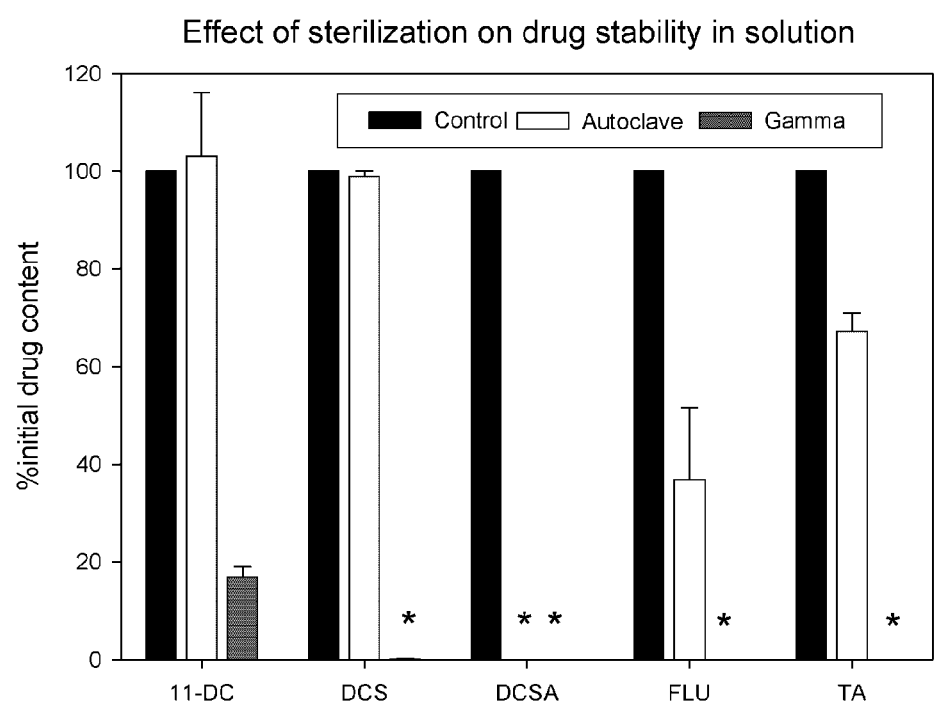
FIG. 3: The effect of autoclave and gamma irradiation sterilization processes on drug stability in aqueous solutions (data are mean±sd, n=3).

From FIG. 3 it is apparent that 11-DC and DSC were stable to autoclave conditions. TA was moderately stable but this was still felt to be possibly unacceptable degradation of the active under these conditions. FLU was also partly degraded to a similar or worse level as TA, while DCSA was completely degraded. Gamma irradiation had a devastating effect on drug concentration with virtually no drug remaining intact for any of the solutions except 11-DC where less than 20% of the initial drug content remained after sterilization.

Figure 4:
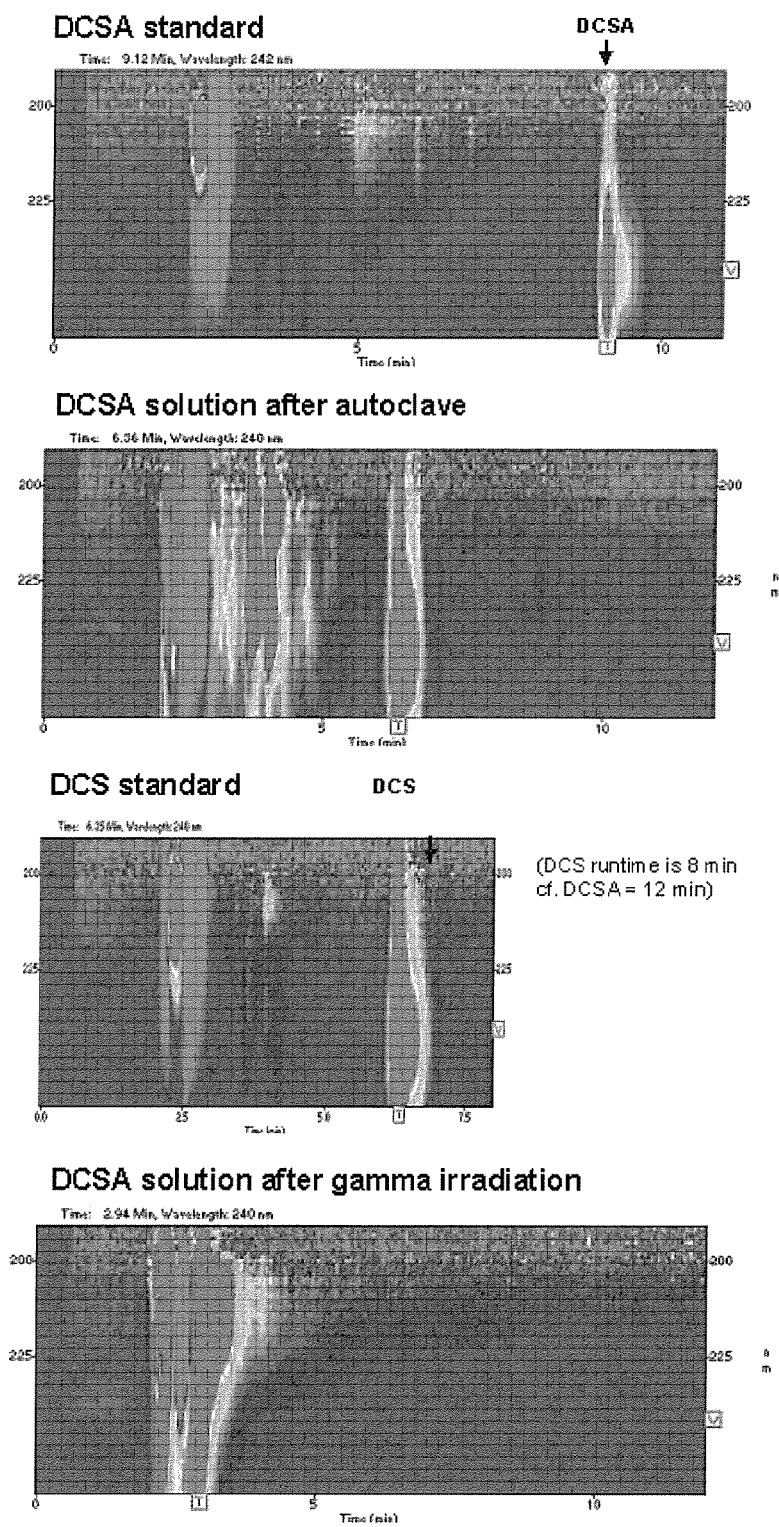
FIG. 4: Contour plots for HPLC with absorption wavelength on the y axis and retention time on the X-axis, the intensity of colour indicates degree of absorbance at that wavelength and retention time ($\lambda$max=240 for all compounds in this study).

The use of a diode array detector allows some interpretation of what is occurring in the samples based on the 3-dimensional absorbance versus wavelength versus retention time plots. In particular, FIG. 4 below indicates that DCSA has been completely degraded to DCS under autoclave conditions, but was completely degraded under gamma irradiation, i.e. no DCS or DCSA were evident in the 3D-contour plot. The degradation of DCSA to DCS is important, as it is necessary to be certain that the pharmacological response in the in vivo studies is due to DCSA and not DCS produced by drug degradation in solution.

Drug Powders

The poor stability of most drugs under either autoclave or gamma irradiation when in contact with aqueous diluent led to a further set of stability studies to test the effect of gamma irradiation on the dry drug powders, with a view to providing the study materials as sterile powders for reconstitution immediately prior to administration.

Figure 5:
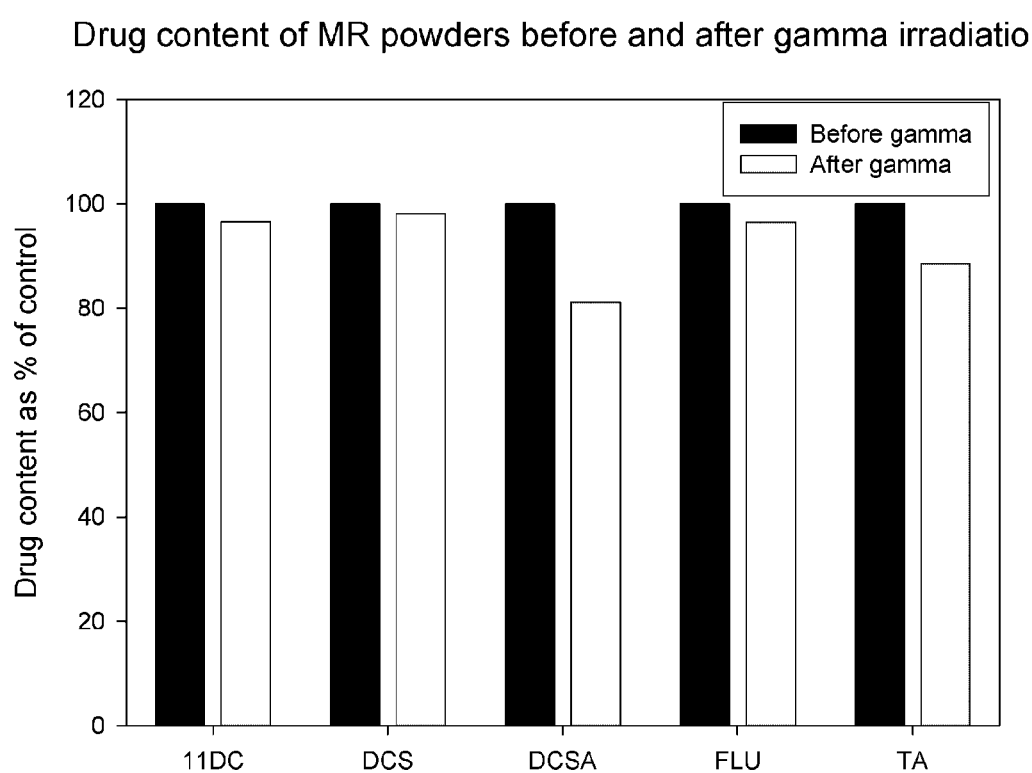
FIG. 5: Stability of MR compounds and TA in dry powder form on exposure to 25 kGy gamma irradiation.

FIG. 5 demonstrates the stability of the powders when subjected to gamma sterilization and assayed for subsequent drug content compared to a similarly handled, non-irradiated control. Only DCSA appeared to demonstrate a slight reduction in drug content, however only one sample was analysed so the difference may be due to inevitable slight systematic error, but is still remarkably high when compared to the data in FIG. 3.

Particle Size and Refinement

It is recommended in the literature that particle size of ocular suspensions should be less than 50 microns and preferably less than 25 microns to avoid irritation to ocular tissues from large crystals of drug. The triamcinolone acetonide and fludrocortisone used in these studies were micronised powders directly from Farmabios; however, the remaining three drugs were obtained from Sigma Alrich as commercial samples that were not micronised. Hence it was of importance to: (i) Characterize the size of the remaining three powders and to confirm that of TA and FLU before proceeding; and (ii) to refine the particle size where required to obtain appropriate sized material to progress to study material development.

Particle Sizing by Laser Light Scattering

Table 2 shows the measured particle size distribution for 'as received' samples of powdered compounds. It is clear that the three non-micronised samples would need further refinement in order to make it suitable for formulation into an injectable intravitreal product.

SEM Imaging of Raw Materials

Figure 6:
FIG. 6: SEM images of MR powders as received. All images are on similar scales, highlighting the gross differences between them.
Figure 6:
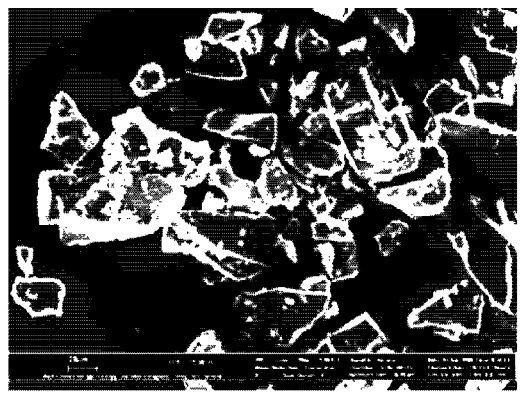
Figure 6:
Figure 6:
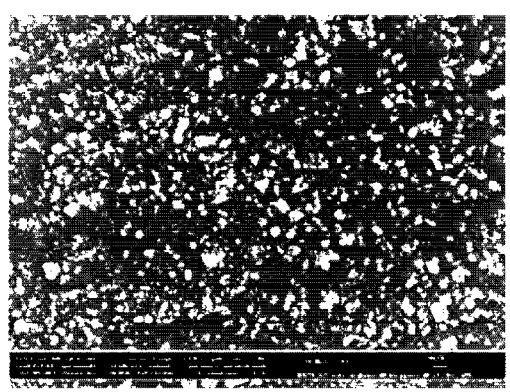
Figure 6:
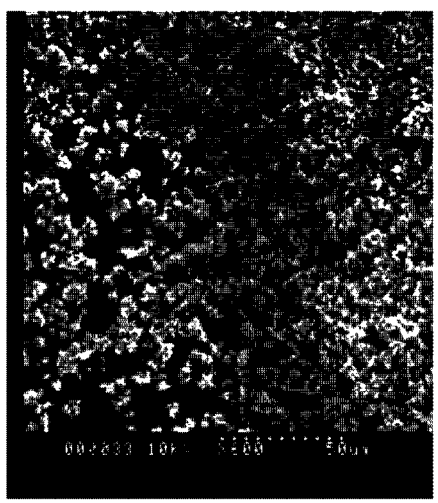

The powders were investigated also by SEM for morphology, aggregation or other phenomena that may not be apparent in laser light scattering. The representative images shown in FIG. 6 agree well with the particle sizing results in the previous section.

It is clear that all three non-micronised powders require refinement to make them suitable for formulation for back of eye applications. It became apparent that with the small quantities of the powders available, the regular methods of ball milling or jet milling would be unlikely to yield adequate results, and very low yields of powder would likely eventuate. It was decided that wet milling with a homogenizer would be the best approach, and a homogeniser was used for the purpose (Polytron).

Figure 7:
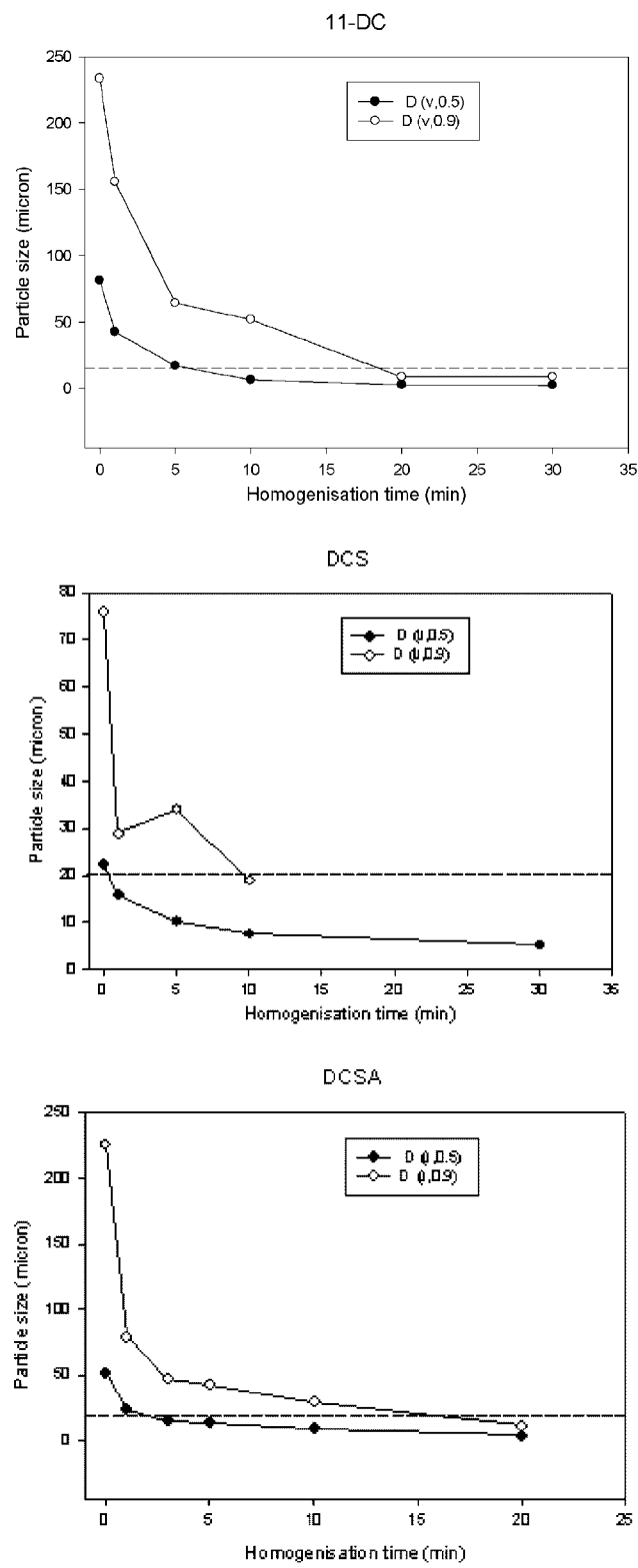
FIG. 7: Reduction in Particle Size (distribution indicated by D(v,0.5) and D(v,0.9)) for 11-DC, DCS and DCSA with homogenisation time.

Samples of 11-DC, DCS and DCSA were prepared as suspensions with 0.4% Tween 80 (also known as Polysorbate 80) as a wetting agent, and homogenised with a Polytron on speed 6 for varying amounts of time to determine the required processing time. As can be seen in the individual plots below in FIG. 7, the process was effective for all drugs. A target D(v,0.9), which indicates the size below which 90% of the particles are represented, was set at 20 micron, and in all cases this was achieved in 20 mins or less processing time, and consequently this method was used for particle refinement for the rest of the formulation development tasks.

Formulation Manufacture Development and Process Optimization

The following intermediate conclusions were adopted in deciding on the final formulation approach. 1. Autoclave and gamma sterilization are not suitable sterilization methods for these compounds when in aqueous form. 2. Gamma sterilization appears to be suitable for powders when in dry form only. 3. The particle size of 11-DC, DCS and DCSA needs to be refined by wet milling to be adequate for these studies.

Thus a broad approach was adopted involving the following stages: Wet sieve drugs Particles to D (V, 0.9) less than 20 μM; Freeze Dry Drug Alone; Add solution of all excipients to drug powder in tube; dispense to vials and freeze dry; gamma sterilize and quality control; reconstitute in BSS at time of study or use.

From Table 3, our conclusion was that all drugs apart of TA without CMC and Tween80 experienced suspendability problems therefore the recommended formulation includes CMC and Tween 80 as shown in Tables 3 and 4.

Consequently, the formulation of Table 4 was utilized for the study materials.

Summary of Batch Production Results Indicating Applicability of Method

Table 5 shows a summary of batch production results. The one failed result had a dose of DCSA in the vial slightly below the lower specification of 18 mg. This is likely due to slight degradation of the active during gamma sterilization, but did not give rise to unidentified peaks in the HPLC chromatograms.

Triesence Composition

Table 6 shows the composition of Triesence as listed directly on the Product Information sheet. Accordingly, one option is to use the above process and the Triesence formulation to prepare fludrocortisone system for reconstitution.

Kenalog Composition

Table 7 shows the composition of Kenalog as listed directly on the Product Information sheet. At the time of manufacture, the air in the container is replaced by nitrogen. Sourced from http://packageinserts.bms.com/pi/pi_kenalog-10.pdf.

A Phase Ib, Study of Safety and Tolerability of Intravitreal Fludrocortisone Acetate (FCA) and Triamcinolone (TA)

Investigational Product, Dose and Route of Administration: Fludrocortisone acetate (FCA) 1 mg/0.1 ml & 2 mg/0.1 ml, Intravitreal (IVT) injection. The identical protocol will be followed with TA.

Rationale for dose: Single dose of 0.1 ml in a concentration of 1 mg/0.1 mL and 2 mg/0.1 mL was selected based on a previous pre-clinical model. There were no signs of retinal toxicity on slit-lamp examination, indirect ophthalmoscopy, or by light microscopy in all eyes injected with 400 μg/0.1 mL, 1 mg/0.1 mL and 2 mg/0.1 mL. However, it was reported 1 case of intravitreal haemorrhage in 4 mg/0.1 mL.

Systemic injection of fludrocortisone acetate has serious mineral corticoid and glucocorticoid side effects such as hypertension, potassium loss, Cushingoid changes, etc. Intravitreal injection fludrocortisone acetate may avoid systemic side effects.

Objectives: To determine safety and tolerability of a single dose IVT injection of 1 mg/0.1 mL and 2 mg/0.1 mL FCA.

Study Population: The study is planned to enroll up to 9 participants.

Study Design: This study is planned to enroll 9 participants to assess dose escalation based on a 3+3 algorithm. Enrolment will stop if >2 patients experience dose-limiting toxicity at any time during the study. Dose-limiting toxicity is defined by intraocular inflammation, elevated IOP (intraocular pressure), reduced vision (loss of ≥15 letters), or haemorrhage within 28 days after injection.

Part 1 involves a single participant to assess safety and tolerability of 1 mg/0.1 mL FCA. This participant will be followed for up to 28 days and reviewed by a safety review committee prior to the recruitment of a further 2 participants treated with 1 mg/0.1 mL FCA totalling in 3 participants in the first cohort.

Part 2 involves a single participant to assess safety and tolerability of 2 mg/0.1 mL FCA. This participant will be followed for up to 28 days and reviewed by an independent safety review committee prior to the recruitment of a further 5 participants treated with 2 mg/0.1 mL FCA totalling in 6 participants in the second cohort.

The sample size (n=9) chosen for this study was selected without formal statistical justification, but the numbers chosen are considered adequate for assessing the study objectives. The sample size was determined on the basis of practical and logistical considerations for a pilot study, and not based on statistical power with regard to hypothesis testing or precision with regard to parameter estimation.

Description of Study Intervention: Fludrocortisone acetate (9-α-Fiuoro-11β. 17α, 21-trihydroxy-4-pregnene-3, 20 dione acetate) is a synthetic steroid possessing a potent mineralocorticoid effect and a high glucocorticoid activity. The physiologic effects of fludrocortisone acetate are similar to hydrocortisone but much more potent. FCA has a glucocorticoid activity ten times higher than cortisol and a mineralocorticoid effect 250 times higher than cortisol. Addition of fluorine to C-9 of cortisol gives fludrocortisone a markedly increase in glucocorticoid, mineralocorticoid and anti-inflammatory potency. The drug will be administered via intravitreal injection.

Study Duration: 6-months' recruitment and 6-month follow-up period.

Participant Duration: Participants will be on the study for 6 months. Screening: up to 14 days Treatment: 1 day. Follow-up: 6 months.

Pharmacokinetic (PK) parameters: Exposure after single dose Fludrocortisone acetate IVT injections; Serum maximum observed concentration; Time to maximum measured concentration; Terminal elimination half-life.

Planned Interim Analysis: There is no formal interim analysis planned for this study. However, a data safety monitoring board (DSMB) for safety data review will be planned for this study.

Analysis Populations—the following analysis populations are planned: Safety Population: all enrolled participants IVT Fludrocortisone acetate will be included in the safety population; intention-to-treat (ITT) Population: all enrolled participants who received IVT Fludrocortisone acetate and had at least one efficacy measurement taken after dosing will be included in the ITT population.

Statistics Analyses—Safety Analysis: Statistical methods for the safety analyses will be primarily descriptive in nature. Listings and summaries for all safety data will be presented using the Safety Population. Descriptive statistics (mean, SD, median, minimum and maximum) will be calculated for summaries of continuous safety data and frequency counts and percentages (where appropriate) will be calculated for summaries of discrete/categorical safety data. Safety data, including vital signs, clinical safety labs and adverse events, will be summarised. Change from baseline will be included in summary tables for vital signs and laboratory parameters. All laboratory data will be included in the data listings and all test values outside the normal range will be flagged. Physical examinations will be listed for each participant. Adverse events (AEs) will be coded using the Medical Dictionary for Regulatory Activities (MedDRA), and data will be summarised by System Organ Class and preferred term.

Categorical efficacy endpoints such as slit lamp biomicroscopy exam findings, dilated ophthalmoscopy exam findings, colour fundus photography and OCT findings will be summarised descriptively by frequency count and percentage (proportion) as appropriate.

Schedule of Activities: this is summarised in Table. 8.

Formulation:

The formulation is manufactured using aseptic processes. It is packaged in glass vials with coated rubber stoppers with plastic flip-off disks and are to be used for single-dose administration only. Part A: 10 mg of Fludrocortisone will be placed in a vial which will be sent off for Gamma Sterilization. Part B: Will be a vial containing the sterile diluent. These processes will be carried out by a trained Pharmacist and Sterile Facility technician in a Grade B Room under a Grade A hood. The investigational product will be produced by an accredited compounding pharmacy under GMP.

Storage and Handling:

Fludrocortisone is formulated for intravitreal administration as a 10 mg powder for solution for injection.

Each vial contains 10 mg of fludrocortisone powder. The diluent consists of Isotonic Sterile Saline (Sodium Chloride solution 0.9%). The fludrocortisone powder for solution for intravitreal injection is reconstituted with 1.0 ml or 0.5 ml of diluent for injection depending on the concentration required. Following reconstitution, the concentration is suitable for delivering at a 1 mg/0.1 ml or 2 mg/0.1 ml dose in 0.1 ml intravitreal injection volume.

The fludrocortisone 10 mg powder for solution and diluent is for single use and must be stored at 2-8° C., protected from light.

Pharmaceutical Form:

Fludrocortisone is formulated for intravitreal administration as a 10 mg powder for solution for injection.

Each vial contains 10 mg of fludrocortisone powder. The diluent consists of Isotonic Sterile Saline (Sodium Chloride solution 0.9%). The fludrocortisone powder for solution for intravitreal injection is reconstituted with 1.0 ml or 0.5 ml of diluent for injection depending on the concentration required. Following reconstitution, the concentration is suitable for delivering at a 1 mg/0.1 ml or 2 mg/0.1 ml dose in 0.1 ml intravitreal injection volume.

The fludrocortisone 10 mg powder for solution and diluent is for single use and must be stored at 2-8° C., protected from light.

Dosage and Administration:

Fludrocortisone may be provided as single-use stoppered glass vials containing sterile fludrocortisone 50 mg. Dry powder fludrocortisone diluted in sterile saline has been injected into one patient. 50 mg sterilised dry powder fludrocortisone was diluted by added 5 ml sterile saline into the vial containing the fludrocortisone. 0.1 ml was injected into any eye.

The indicated IVT dose of fludrocortisone will be administered by one intravitreal injection of up to 0.1 ml of 1 mg/0.1 ml and 2 mg/0.1 ml fludrocortisone.

Intravitreal Toxicology:

Intravitreal doses of Fludrocortisone acetate of 0 (vehicle control), 400 µg, 1 mg, 2 mg, 4 mg/eye were tested in a study of New Zealand albino rabbits.

All animals were examined before and after injection using the indirect ophthalmoscope and slit-lamp biomicroscopy. Electroretinography (ERG) was performed on all animals before intravitreal injection and two weeks after injection. The animals were re-examined at this time by indirect ophthalmoscopy and slit-lamp biomicroscopy and were euthanized. The eyes were enucleated and examined with light microscopy.

One eye in the 4 mg/0.1 ml fludrocortisone group exhibited significant decreases in ERG; one eye of this group had a vitreous hemorrhage. There was no significant decrease in ERG in the other groups. There were no signs of retinal toxicity on slit-lamp examination, indirect ophthalmoscopy, or by light microscopy in all eyes injected with 4 mg/0.1 ml or less of fludrocortisone. Intravitreal injections of fludrocortisone at 2 mg/0.1 ml appeared safe in albino rabbit eyes.

Animal Studies

An animal study was conducted to evaluate the safety and efficiency of Fludrocortisone acetate after intravitreal injection into the vitreous cavity [see Kivilcim, M., et al., Evaluation of the Retinal Toxicity of Fludrocortisone Acetate After Intravitreal Injection. Investigative Ophthalmology & Visual Science, 2006. 47(13): p. 4281-4281]. Surgeries were performed on the eyes of 25 New Zealand white rabbits. Fludrocortisone acetate was titrated using sterile BSS solution to the following concentrations: 4 mg/0.1 ml, 2 mg/0.1 ml, 1 mg/0.1 ml, and 400 µg/0.1 ml, which were injected intravitreal into one eye of twenty-five rabbit eyes. The control eyes received 0.1 ml of sterile BSS. All animals were examined before and after injection using indirect ophthalmoscope and slit-lamp biomicroscopy. Electroretinography (ERG) was performed on all animals prior to intravitreal injection and two weeks after injection. The animals were re-examined at this time by indirect ophthalmoscope and slit-lamp biomicroscopy and were euthanized. Their eyes were enucleated and examined with light microscopy.

Outcomes from these in vivo tests were positive for the application of intravitreal fludrocortisone acetate. In multiple measurements, up to 40 days of observations, the slit lamp biomicroscopy and indirect ophthalmoscopy did not show any evidence of significant inflammation in the anterior or posterior segment of the eye in either the control or treatment groups. IOP was normal across all groups.

Histological examination of retinal sections, under light microscopy, revealed that the integrity of the retinal layers appeared preserved with no evidence of toxicity or vacuolization except for one eye in the 4 mg group. All aggregates of fludrocortisone acetate disappeared by 22+/−8 days in the 2-mg group, and 33+/−7 days in the 4-mg group.

In ERG testing, one eye injected with 4 mg/0.1 ml exhibited decreases in ERG output. All other eyes had a normal ERG. These findings represent promising results for intravitreal Fludrocortisone acetate that is clinically suitable for both short-term and long-term use.

Rationale:
Rationale for this Study:

Fludrocortisone acetate is available in tablet form (0.1 mg) from the PBS and so is approved for use in humans in Australia. In a study of 121 patients, excellent outcomes with fludrocortisone for anterior segment lesions were reported (see Gonzalez, C., Topical fludrocortisone (9-*alpha fluorohydrocortisone*) in ophthalmology. Am J Ophthalmol, 1960. 49: p. 619-22). This document cited 4 previous papers with similar experiences.

There is older pre-clinical data suggesting FCA is effective. Among that is Fitzgerald et al. who found that FCA was superior to TA in a study of phorbol-12-myristate-acetate (PMA)-stimulated monkey choroidal endothelial cells (CECs) in restoring quiescent morphology and reducing membrane permeability (Fitzgerald, M., et al., *Mineralocorticoids restore quiescent morphology and reduce VEGF receptor expression in inflamed choroidal endothelial cells in vitro*. Ophthalmic Res, 2009. 41(1): p. 44-52). Prof Jan Provis et al. have a large body of new preclinical data that indicates FCA is superior to TA in a rat model of dry AMD. FCA was superior in terms of preventing cell death, macrophage recruitment, and preserving a- and b-wave ERG amplitude.

Kivilcim cited above, examined intravitreal FCA in 25 normal rabbits at 4 mg/0.1 ml, 2 mg/0.1 ml, 1 mg/0.1 ml, and 400 µg/0.1 ml. Two eyes at 4 mg/0.1 ml experienced intravitreal haemorrhage and reduced ERG. There were no other problems of reductions in ERG. The smaller volume of the rabbit eye would suggest 4 mg/0.1 ml would be safe in humans. TA is commonly given at 4 mg/0.1 ml so comparing the same doses for each steroid would be sensible.

Dose Selection:

A single dose of 1 mg/0.1 mL or 2 mg/0.1 mL injection administered once will be tested in this study.

Intravitreal fludrocortisone acetate was well-tolerated in a panel of animal toxicology studies. The volume of the human vitreous is approximately 4 mL, which is approximately 2.7-fold larger than the mean vitreous volume of rabbits, 1.5 mL. Based on the difference in vitreous volume between man and rabbit, the human equivalent dose was determined to be 67 mg/eye every 4 weeks. The dose (1- or 2 mg/0.1 mL injection) of fludrocortisone acetate that will be evaluated in this clinical study is expected to result in drug concentrations approximately 1.3 fold lower than observed in rabbits.

Risk/Benefit:

The safety monitoring practices employed by this protocol (e.g. complete ophthalmologic exam, IOP monitoring, OCT, vital signs, hematology, serum chemistry, and AE questioning) are adequate to protect the subjects' safety.

There are risks associated with the ophthalmic procedures required for participants in this study. However, these are all standard procedures that are widely performed in ophthalmology.

In the days following any IVT injection, patients are at risk of developing endophthalmitis. If the eye should become red, sensitive to light, painful, or develop a change in vision, the patient will be instructed to seek immediate care from an ophthalmologist. Other risks of IVT injection include traumatic cataract, retinal detachment and hemorrhage.

Transient increased IOP has also been identified as a risk following IVT injections. IOP will be carefully monitored in this study.

The approximately 150 mL of blood planned for collection from each subject over the 6 months of the study does not pose an undue risk in this patient population.

Based on data available to date, IVT administration of fludrocortisone acetate does not seem to present an unreasonable ophthalmic or systemic risk in animal models. Fludrocortisone acetate has been safely used systemically as mineralocorticoid replacement for severe orthostatic hypotension in Addison's disease and other salt-water disbalances.

However, as fludrocortisone acetate has not been used intravitreally in human participants there are potential unforeseen risks. To mitigate such risks, this study is being conducted in two parts, restricting treatment to a single individual together with extended assessment, prior to application in other participants. Numerous follow-up visits and numbers of testing procedures have also been instituted in the assessment schedule for all participants to ensure adverse events, or other safety issues that arise are identified and addressed in a timely manner.

There is a potential health benefit for trial participants from receipt of study drug. We propose to administer intravitreal fludrocortisone acetate. If efficacious, intravitreal fludrocortisone acetate is expected to alter the course eye disease and slow its rate of progression.

Objectives and Endpoints:
Study Objectives:

The primary objectives of the study are to assess the safety and tolerability of IVT injections of Fludrocortisone acetate in order to support further development into confirmatory Phase II studies.

Study Endpoints:
Primary Safety Endpoint:

To demonstrate safety and tolerability of IVT injections of Fludrocortisone acetate number and severity of local and systemic treatment emergent adverse events.

Secondary Endpoints:

Change in best corrected visual acuity (BCVA) Change in low luminance best corrected visual acuity (LL-BCVA). Change in vital signs. Increase in IOP. Pharmacokinetic (PK) parameters. Exposure after single dose fludrocortisone acetate IVT injections. Serum maximum observed concentration. Time to maximum measured concentration. Terminal elimination half-life.

Study Population:

The study population includes approximately 9 (n=9) subjects to be enrolled at approximately one (1) site. If both eyes have the same visual acuity, the right eye will be used as the study eye.

The complete inclusion and exclusion criteria are presented above.

Women of Childbearing Potential (WOCBP):

WOCBP are defined as pre-menopausal women physiologically capable of becoming pregnant.

Women of Non-Childbearing Potential:

WONCBP are defined as women meeting any of the following criteria: Older than 45 years with amenorrhea for >2 years or older than 60 years with amenorrhea for >1 year, both confirmed by FSH and LH levels; Has undergone hysterectomy; Has undergone bilateral oophorectomy; and Has undergone bilateral salpingectomy.

Approved Methods of Contraception:

Approved methods of contraception include: oral contraceptives, intrauterine device, medically acceptable barrier methods (i.e. condom), implantable or injectable contraceptives or removable birth control device. Subjects practicing abstinence and coitus interruptus (pull out method) must agree to use an approved method of contraception during the study Treatment of Subjects:
Allocation of Treatment:

Each subject will be assigned a unique screening number before screening. Subjects who complete the study screening assessments and meet all the eligibility criteria will be scheduled to enter the study and will receive treatment with intravitreal fludrocortisone acetate on Day 0.

Treatments Administered:
Dose Levels and Study Arms:

A single dose of 1- and 2 mg Fludrocortisone acetate/0.1 mL will be tested in this study.

Subjects will receive 1 IVT injection as outlined in Table 9.

Drug Supplies:
Identity of Investigational Product

Fludrocortisone acetate is formulated for intravitreal administration as a 50 mg powder for solution for injection.

Each vial contains 50 mg of fludrocortisone powder. The diluent consists of Sodium Chloride solution (0.9%) quantity sufficient to 100%. The fludrocortisone powder for solution for intravitreal injection is reconstituted with 1.0 ml and 0.5 ml diluent for injection dependent upon concentration required. Following reconstitution, the concentration is suitable for delivering at a 1 mg/0.1 ml or 2 mg/0.1 ml dose in 0.1 ml intravitreal injection volume.

The fludrocortisone acetate 50 mg powder for solution and diluent is for single use and must be stored at 2 to 8° C., protected from light.

Accountability:

IVT Fludrocortisone acetate drug product will be provided to a designee at the study site and must be stored in a pharmacy or otherwise locked and secured, at temperatures between 2° C. and 8° C. in a refrigerated area with limited, controlled access and temperature monitoring; do not freeze. IVT Fludrocortisone acetate drug should be protected from light by storing in the carton provided. The drug product supply is accessible only to those individuals authorized by the PI. The Sponsor will supply sufficient quantities of fludrocortisone acetate drug product to allow completion of this study.

Designated study staff will provide the study treatments to the subjects in accordance with their assigned subject numbers and the randomization schedule. During the study, the receipt of the drugs supplied at the clinical site and of study treatment dispensation for each subject will be documented in drug accountability records. These drug accountability records are to be kept separate from the patient medical records and other source documents.

All used vials should be retained by the clinical site until drug accountability monitoring is performed and then returned to the Sponsor or designee, or destroyed per Sponsor instructions.

At the conclusion of the study, any unused investigational product will be retained by the clinical site, returned to the Sponsor or designee, or destroyed per Sponsor instructions, and this will be documented in the drug accountability records.

Intravitreal Fludrocortisone Acetate Administration:

Subjects receiving active treatment will be administered a 1 mg/0.1 ml or 2 mg/0.1 mL IVT injection of Fludrocortisone acetate using a 27 G thin wall needle, at the discretion of the PI.

Clinic staff involved in the injection tray assembly, anaesthetic preparation, and study drug preparation and administration will follow appropriate aseptic techniques to minimize the risk of potential adverse events associated with IVT injections (e.g. endophthalmitis).

The investigation drug will be presented in a kit containing 1×1 ml syringe with 27 g 12 mm needle, 1×5 ml vial containing sterile fludrocortisone 10 mg, 1×Vial containing 2 ml Diluent for reconstitution and alcohol swab to swab top of vials before puncturing bungs.

Preparation of the solution: The injecting doctor will withdraw 1.0 ml or 0.5 ml of diluent and reconstitute the powder. The doctor will then draw up 0.1 ml of the fluid ready for injection.

To minimize IOP elevation after IVT injection of fludrocortisone acetate, decompression of the eye must be performed before all fludrocortisone acetate injections. This is done by applying moderate pressure to the globe with cotton swabs for 30-60 seconds during aesthetic preparation.

In addition to the procedures outlined in this protocol, adherence to specific institutional policies associated with IVT injections will be observed.

Concomitant Therapies:

Any concomitant medications a participant is receiving at the start of the study or that are given for any reason during the study (except for routine medications given for ocular procedures required by the protocol, such as topical aesthetic) must be recorded in the source document and CRF including start and stop date and time, dose, route, and indication. In addition, all ocular and non-ocular procedures such as surgical procedures (excluding study treatment procedures) must also be recorded in the source document including start and stop dates. Surgical anaesthetics, paramedical or alternative therapies (e.g. acupuncture, massage) should also be recorded in the source documents and CRF. Metoclopramide or other agents to prevent nausea induced by fluorescein injection may be administered at the discretion of the PI.

Endophthalmitis Treatment:

The decision to treat a participant for endophthalmitis or suspected endophthalmitis will be guided by the clinical judgment of the PI. The treatment method (pars plana vitrectomy vs. vitreous tap) and choice of antimicrobial agents are also at the discretion of the PI and should follow current standard practice patterns. The decision to use IVT steroids (e.g. dexamethasone) for the treatment of endophthalmitis is also at the discretion of the PI.

Study Procedures:

Study Design:

This is a Phase Ib study to assess the safety and tolerability of a single dose of IVT injection of fludrocortisone acetate.

The study is planned to enroll an initial cohort of 3 patients in a dose of 1 mg/0.1 mL. A total of 9 participants can be included to assess dose escalation based on 3+3 algorithm.

Patients should be screened up to 14 days before receiving Fludrocortisone acetate. Upon entry into the study, patients will be assigned a subject screening number. Subjects who meet all inclusion and exclusion criteria and are confirmed as eligible by the CRC will return to the clinic for the administration of single dose IVT Fludrocortisone acetate (Day 0) as outlined below.

All subjects will return to the clinical site on Day 1 and Day 7 to assess acute safety after the injection. After that, all subjects will return for another 6 follow-up visits and 6 months after the injection. See Study Outline below.

Safety will be assessed throughout the study; serial blood samples and urine samples will be collected. Blood samples will also be collected for the PK assessment of fludrocortisone acetate.

The planned length of participation in the study for each subject is approximately 6 months (from Day 0-through completion of the Month 6 (Day 150) follow-up procedures).

The study is planned to take place over approximately 12 months (from screening of the first subject through completion of the last subject's exit visit).

Subject Enrollment:

It is the responsibility of the investigator to ensure that subjects are eligible to participate in the study prior to enrollment and throughout the study. Documentation of the personally signed and dated informed consent of each subject, using the study-specific ICF, is required before initiating the Screening process. After written informed consent has been obtained and eligibility to participate established, investigative site personnel will obtain the subject's identification number. Only eligible subjects will be allocated to the open label FCA 1 mg/0.1 mL or 2 mg/0.1 mL.

Enrolment will occur in two parts in order in order to minimise the likelihood that subjects will be exposed to risks. During part 1 & 2, subjects will be screened one by one as only one patient will initially be enrolled during part 1 of the trial. The first enrolled subject will participate in a screening period of up to 14 days and a follow-up period of 28 days, to detect an IOP response.

After the first subject has completed the follow-up of 28 days after FCA 1 mg/0.1 mL injection, The subject's safety data will be reviewed the safety data of this will be reviewed by an independent safety review committee to determine whether to commence enrolment of additional 2 patients in the first cohort of 1 mg/0.1 mL dose of FCA. Enrolment will be stopped if >2 patients experience limiting-toxicity adverse event related to the study drug. If no more than two adverse events considered to be related to the study drug occur with limiting toxicity, the second cohort will be recruited. Dose-limiting toxicity is defined by intraocular inflammation, elevated IOP, reduced vision (loss of ≥15 letters), or haemorrhage within 28 days after injection.

Part 2 will take in place if the 3 subjects have tolerated well the dose. Part 2 initially involves a single subject treated with 2 mg/0.1 mL FCA to assess safety and tolerability. This subject will be followed for up to 28 days and reviewed by an independent safety review committee prior to the recruitment of a further 5 subjects treated with 2 mg/0.1 mL FCA totaling in 6 subjects in the second cohort.

Meeting minutes will be generated at each meeting and included in the sponsor's study files. Formal reports will not be prepared prior to or following these meetings. As general guidance, a subject will be considered to have tolerated a dose if the subject experiences no clinically significant drug-related adverse event or laboratory abnormality. Conversely, a subject will not be considered to have tolerated the dose if he experiences a clinically significant drug-related adverse event or laboratory abnormality during the study drug administration or post-administration follow-up period Safety to cataract will be reviewed among all participants at the 150 day review.

It is understood that safety is a medical judgment that cannot be prospectively defined in detail. Subjects will be closely monitored with clinical observations and safety laboratory testing.

Study Visit Schedule

Below is a condensed description of the study visits and the procedures and examinations that will be performed. Please refer to the Schedule of Activities (SoA) table for a detailed schedule of procedures/assessments for the Monthly visit schedules. Additional safety assessments not listed herein may be performed if considered necessary at the discretion of the PI.

Screening—within 14 Days Prior to Treatment

Visit 1—All Subjects: All ophthalmic procedures (including imaging) are to be performed on both eyes:

1. Before any study specific procedures are performed, explain the purpose and nature of the study, and have the patient read, sign, and date the Institutional Review Board/Independent Ethics Committee (IRB/IEC)—approved Informed Consent Form (ICF). Have the individual obtaining consent from the patient and a witness, if applicable, sign and date the ICF. 2. Obtain a screening number for the subject. 3. Obtain information on demographics, medical/ocular history, and concomitant medications used 90 days prior to enrolment. Include vitamins, and all over-the-counter as well as prescription medications. 4. Screen the patient for inclusion/exclusion criteria. 5. Collect blood (including blood for HCG/FSH/LH, if applicable) and urine for laboratory analysis and forward the samples to the central laboratory. 6. Collect vital signs. 7. Perform BCVA. 8. Perform LL-BCVA. 9. Perform a complete ophthalmic exam including slit-lamp exam of the cornea, iris, anterior chamber, lens (LOCS III if any opacity on the lens noted) and aqueous reaction (cells and flare), dilated fundus exam of the vitreous and retina and IOP measurement. 10. Perform SD-OCT imaging for determination of eligibility by the PI. 11. Perform FAF imaging for determination of eligibility by the PI. 12. Perform NIFR imaging. 13. Perform DCFP for determination of eligibility by the PI. 14. Perform FA for determination of eligibility by the PI.

Visit 2 (Baseline)—All subjects: Unless specified, all ophthalmic procedures (including imaging) are to be performed on the Study eye only. 1. Verify that all inclusion/exclusion criteria are met, including the determination of eligibility by the PI. 2. Obtain information on any changes in medical health and/or the use of concomitant medications. 3. Collect vital signs pre- and post-dose. Vital signs will be measured within 1 hour prior to dosing for the pre-dose time point. Post-dose vital signs readings will be performed within 30 minutes after dosing. 4. Perform BCVA. 5. Perform LL-BCVA. 6. Perform a complete ophthalmic exam including slit-lamp exam of the cornea, iris, anterior chamber, lens (LOCS III if any opacity on the lens noted) and aqueous reaction (cells and flare), dilated fundus exam of the vitreous and retina and IOP measurement. 7. Perform the IVT injection of fludrocortisone acetate. 8. Monitor the study eye within 15 minutes' post injection. 9. Monitor for adverse events.

Visit 3 (Day 1): All Subjects. Post-initial treatment examination:

Unless specified, all ophthalmic procedures (including imaging) are to be performed on the study eye only. 1. Obtain information on any changes in medical health and/or the use of concomitant medications. 2. Collect vital signs. 3. Perform BCVA. 4. Perform LL-BCVA. 5. Perform a complete ophthalmic exam including slit-lamp exam of the cornea, iris, anterior chamber, lens (LOCS III if any opacity on the lens noted) and aqueous reaction (cells and flare), dilated fundus exam of the vitreous and retina and IOP measurement.

Monitor for Adverse Events:

Follow-up Visits—Day 7, 14, 28, 60, 90: Unless specified, all ophthalmic procedures (including imaging) are to be performed on the study eye only. The following procedures will be performed at all follow-up visits: 1. Obtain information on any changes in medical health and/or the use of concomitant medications. 2. Collect vital signs 3. Collect blood for PK analysis (days 7, 28 and 90 only). 4. Perform a complete ophthalmic exam including slit-lamp exam of the cornea, iris, anterior chamber, lens (LOCS III if any opacity on the lens noted) and aqueous reaction (cells and flare), dilated fundus exam of the vitreous and retina and IOP measurement. 5. Monitor for adverse events Termination Visit (or Early Termination)—Day 150: All ophthalmic procedures are to be performed on BOTH EYES. 1. Obtain information on any changes in medical health and/or the use of concomitant medications. 2. Collect blood and urine for laboratory analysis and forward the samples to the central laboratory. 3. Collect blood for PK analysis. 4. Collect vital signs. 5. Perform urine pregnancy test.—WOCBP only.

6. Perform BCVA. 7. Perform a complete ophthalmic exam including slit-lamp exam of the cornea, iris, anterior chamber, lens (LOCS III if any opacity on the lens noted) and aqueous reaction (cells and flare), dilated fundus exam of the vitreous and retina and IOP measurement. 7. Perform SD-OCT imaging. 8. Perform FAF imaging. 9. Perform NIFR imaging. 10. Perform DCFP. 11. Perform FA imaging. 12. Monitor for adverse events Unscheduled Visit:

If a subject return to the clinical site before their next scheduled visit for an assessment of an adverse event or at the request of the PI, all assessments completed at the Unscheduled Visit should be documented in the patient source record and in the eCRF.

Lost to Follow-Up:

A participant will be considered lost to follow-up if he or she fails to return for ≥1 scheduled visits and is unable to be contacted by the study site staff.

The following actions must be taken if a participant fails to return to the clinic for a required study visit:

The site will attempt to contact the participant and reschedule the missed visit within one week and counsel the participant on the importance of maintaining the assigned visit schedule and ascertain if the participant wishes to and/or should continue in the study.

Before a participant is deemed lost to follow-up, the investigator or designee will make every effort to regain contact with the participant (where possible, 3 telephone calls and, if necessary, a certified letter to the participant's last known mailing address or local equivalent methods). These contact attempts should be documented in the participant's medical record or study file.

Should the participant continue to be unreachable, he or she will be considered to have withdrawn from the study with a primary reason of lost to follow-up.]

Study Assessments and Procedures

The following evaluations will be performed during the study outlined in the Schedule of Activities.

Informed Consent Procedures

The Principal Investigator(s) at each site will ensure that the subject is given full and adequate oral and written information about the nature, purpose, and possible risk and benefit of the study. Subjects must also be notified that they are free to discontinue from the study at any time. The subject should be given the opportunity to ask questions and allowed time to consider the information provided.

The subject's signed and dated informed consent must be obtained before conducting any study procedures.

The Principal Investigator(s) must maintain the original, signed Informed Consent Form. A copy of the signed Informed Consent Form must be given to the subject.

Vital Signs

On injection visit, vital signs will be measured within 1 hour prior to dosing and within 30 minutes after dosing.

Vital signs will be measured before venipuncture. Vital signs include blood pressure (BP) and pulse measurements. After the patient has been sitting for 3 minutes, with back supported and both feet placed on the floor, systolic and diastolic BP will be measured using an automated validated device, with an appropriately sized cuff. In case the cuff sizes available are not large enough for the patient's arm circumference, a sphygmomanometer with an appropriately sized cuff may be used. If vital signs are out-of-range at screening/eligibility, the Investigator may obtain two additional readings, so that a total of up to three consecutive assessments are made, with the patient seated quietly for approximately five minutes preceding each repeat assessment. At least the last reading must be within the ranges provided above in order for the patient to qualify. All of the above tests will be performed after resting for 3 minutes at all visits.

Height in centimetres (cm) and body weight (to the nearest 0.1 kilogram [kg] in indoor clothing, but without shoes) will be measured at Visit 1 (Screening). Body mass index (BMI) will be calculated using the following formula: BMI=Body weight (kg)/[Height (m)]2.

Laboratory Analysis of Blood and Urine

Collection of blood and urine will occur at the study site and the samples will be shipped to a central laboratory for analysis.

The following clinical labs will be performed: Hematology: Hemoglobin; Hematocrit; Red blood cell (RBC) count; Platelet count; white blood cell (WBC) count with differential; Chemistry: Blood urea nitrogen (BUN); Creatinine; Bilirubin (total, direct and indirect); Albumin; Alkaline phosphatase (ALP); Aspartate aminotransferase (AST); Alanine aminotransferase (ALT); Creatine kinase; Glucose; Electrolytes (sodium, potassium, chloride, bicarbonate); Urinalysis: pH; Specific gravity; Protein; Glucose; Ketones; Bilirubin; Blood; Nitrite; Urobilinogen; Leukocyte esterase; Other: Human chorionic gonadotropin (HCG) a; Follicle-stimulating hormone (FSH) b; Luteinizing hormone (LH) b.

The Investigator must review the results of the Screening Visit clinical laboratory tests (including recheck results) and confirm that these results do not show evidence of any medical condition that would make study participation inappropriate. The Investigator should also assess any changes from baseline at the follow up visits and the Exit Visit.

Notes: a. Serum Pregnancy Test (i.e. HCG) will be performed for females of child bearing potential at screening only. b. FSH and LH will be performed for postmenopausal females at screening only.

Urine Pregnancy Test

Urine pregnancy test will be performed in WOCBP only as outlined in the Study Flow Chart.

Best-Corrected Visual Acuity

Best-corrected visual acuity (including LL-BCVA) testing, performed by a certified VA examiner, should precede any examination requiring administration of eye drops to dilate the eye or any examination requiring contact with the eye. ETDRS best-corrected visual acuity (BCVA) will be obtained in each eye separately at screening (Visit 1). This assessment is to be performed prior to pupil dilation. The number of letters read correctly (for each eye) will be recorded in the appropriate study document. For the remainder of study visits (Visits 2-8), BCVA will only be obtained in the study eye.

Complete Ophthalmic Exam

The complete ophthalmic exam will consist of the following: External examination of the eye and adnexa; Routine screening for eyelids/pupil responsiveness (including ptosis, abnormal pupil shape, unequal pupils, abnormal reaction to light and afferent pupillary defect); Slit-lamp examination [cornea, anterior chamber, iris, lens, aqueous reaction (cells and flare). If an abnormal lens finding is noted during the slit-lamp examination, at any visit, then the finding should be further characterized with LOCS III. All subsequent visits for that subject should include LOCS III. A complete description of LOCS III standardized procedures and grading scales is outlined in the MOP; Dilated fundus exam including evaluation of retina and vitreous (i.e. posterior segment abnormalities, retinal hemorrhage/detachment, and vitreal hemorrhage density and vitreous cells); Vitreal hemorrhage density and vitreous cells grading scales; Intraocular pressure (TOP) will be measured in both eyes at Visit 1 as per the study site's regular practice and recorded in the appropriate study document. For the remainder of study visits (Visits 2-9), IOP will only be obtained in the study eye.

Ocular Imaging

The following ocular images will be obtained as outlined in the visit schedule above, also see SOA: Digital Color Fundus Photograph; Fluorescein angiography; Spectral Domain Optical coherence tomography; Fundus Autofluorescence; Infrared reflectance imaging. Only done at selected clinical sites with Heidelberg Spectralis® system.

Post-Injection Assessment

The study eye will be assessed before and after injection to ensure that the injection procedure and/or the study medication have not endangered the health of the eye. The initial post-injection assessment should be done within 15 minutes post-injection and include a gross assessment of vision (light perception) and monitoring IOP. If subject passes gross vision test and IOP is <30 mmHg, the subject may leave the site. If subject fails gross vision test and/or IOP is >30 mmHg, assessments will continue every approximately 30 minutes until the subject passes gross vision test and IOP is 30 mmHg.

Any subject who develops a significant and sustained raise in IOP (>30 mmHg) or a non-adequately perfused central retinal artery (CRA) after injection, should be monitored according to the PI's clinical judgment and may undergo additional procedures and measurements of IOP beyond those specified in the protocol as well as IOP lowering procedures. If any concern or immediate toxicity is noted, the subject will remain at the site and will be treated according to the PI's clinical judgment.

Blood Volume for Study Assessments

Blood volume during study (up to Day 150), see Table 10.

Adverse Events and Serious Adverse Events

All adverse events (AEs) (as defined above), either observed by the PI or one of their medical collaborators, or reported by the participant spontaneously, or in response to direct questioning, will be reported. All adverse events (ocular, non-ocular, serious, non-serious, volunteered, and elicited) must be documented in study records.

Definition of Adverse Events (AE)

An adverse event is any untoward medical occurrence in a subject who receives a pharmaceutical product. The occurrence does not necessarily have to have a causal relationship with the treatment. Therefore, an AE can be any unfavorable and unintended sign, symptom, or disease temporally associated with the use of a drug, whether or not considered related to the drug.

Note: For purposes of this study, abnormal laboratory values will not be considered adverse events unless deemed clinically significant by the Investigator. All abnormal laboratory values will be recorded in the database and appropriate analyses presented in the final study report.

Definition of Serious Adverse Events (Se)

A serious adverse event (SAE) is defined as any untoward medical occurrence that at any dose: Results in death; is life-threatening: this means that the subject was at risk of death at the time of the event; it does not mean that the event might have caused death had it occurred in a more severe form; Required hospitalization or prolongation of existing hospitalization; results in persistent or significant incapacity or substantial disruption of the ability to conduct normal life functions; or is a congenital anomaly or birth defect.

Important medical events that may not result in death, be life-threatening, or require hospitalization may be considered serious when, based upon appropriate medical judgment, they may jeopardize the patient or subject and may require medical or surgical intervention to prevent one of the outcomes listed in the above definition.

Medical and scientific judgment should be exercised in deciding if an AE is serious and if expedited reporting is appropriate.

Adverse Events of Special Interest

An adverse event of special interest is one of scientific and medical concern specific to the Sponsor's product or program where ongoing monitoring and rapid communication by the Investigator to the Sponsor may be appropriate. These adverse events may be serious or non-serious. Applicable adverse events may require further investigation in order to characterize and understand, and depending upon the nature of the event, rapid communication by the trial Sponsor to other parties may also be required. These adverse events of special interest must be reported using the same mechanism and timeframe (i.e. within one working day of the Investigator's or delegate's knowledge of the event) as described for serious adverse events. The adverse events of special interest include the following: Endophthalmitis; 4+ ocular inflammation; 2-3+ ocular inflammation that fails to decrease to 1+ or less within 30 days of the onset of the event; Sustained (>5 minutes) loss of light perception after FCA injection; Sustained elevation of IOP (30 mmHg) at/past 90 minutes' post-injection; Any elevation of IOP requiring surgical intervention (i.e. paracentesis); new vitreous hemorrhage of >2+ severity that does not resolve within 14 days of the onset of the even; cataract progression.

If an adverse event of special interest occurs in a study subject, the study subject will be followed for resolution of the adverse event. A decision will be made by the Sponsor concerning further exposure to the study treatment and further participation in the study.

Adverse Event Assessment and Recording

The Investigator will probe, via discussion with the subject, for the occurrence of AEs during each subject visit and record the information in the site's source documents. For each AE, the PI should note the start and resolution dates, the severity, whether it meets the definition of an SAE, the relationship of the event to the study drug, the action taken regarding study drug, and the outcome of the event. Data should be transcribed from the source documents to the CRF as per the CRF instructions.

When reporting an adverse event, the event description should use the best matching terminology describing the event as found in the "Common Terminology Criteria for Adverse Events" (CTCAE, v 4.03). If an available CTCAE term fits the event well, no additional descriptors may be needed.

However, the Investigator should add any necessary descriptions in order to clarify the event or to place it in an appropriate context. If an appropriate term matching the adverse event cannot be found in the CTCAE and you do not know the preferred MedDRA term, the adverse event description should include a diagnosis, sign or symptom with additional information to facilitate subsequent categorization into MedDRA coding terms Intensity The PI must grade the severity of all reported adverse events into one of five categories: Grade 1 (Mild), Grade 2 (Moderate), Grade 3 (Severe), Grade 4 (Life-Threatening) or Grade 5 (Death related to AE). The standardized CTCAE severity grading scales for the specific type of adverse event reported must be used when a matching CTCAE term is available. If no reference to a standard grading scale applies or is immediately available, use the following guideline:

GRADE 1—MILD: Persistence of any otherwise insignificant medical occurrence beyond 72 hours or any transient (<72 hours) AE considered by the PI to be related to the study drug. No or minimal medical therapy or intervention required, hospitalization not necessary, no or little limitation in normal activities; non-prescription or single-use prescription therapy may be employed to relieve symptoms. Mild adverse events may be listed as expected consequences of the therapy for any given protocol, and standard supportive measures for such an expected event do not necessarily elevate the event to a higher grade.

GRADE 2—MODERATE: Mild to moderate limitation in activity, some assistance may be needed; possibly none but usually minimal intervention/therapy required, hospitalization possible.

GRADE 3—SEVERE: Marked limitation in activity, some assistance usually required; medical intervention/therapy required; hospitalization possible or likely. [Specifically, for ocular adverse events in this vision related study, an immediately sight-threatening condition (e.g., impending corneal perforation, retinal detachment) may be categorized as Grade 3 if it would lead to total blindness in the affected eye(s).]

GRADE 4—LIFE THREATENING: Extreme limitation in activity, significant and immediate assistance required; significant medical/therapy intervention required to prevent loss of life; hospitalization, emergency treatment or hospice care probable. This grade is used when the participant was, in the view of the PI, at substantial risk of dying at the time of the adverse event or it was suspected that use or continued use of the test article would have resulted in the participant's death. (This does not include a reaction that, had it occurred in a more serious form, might have caused death. For example, drug-induced hepatitis that resolved without evidence of hepatic failure would not be considered life-threatening even though drug-induced hepatitis can be fatal.)

GRADE 5—DEATH: Death related to AE.

Causality:

The PI (or an authorized study physician) must submit an attribution for causality of the reported adverse event to the test article or procedure.

The attribution should take into account both the temporal association and any known physical, physiological or toxicological information regarding the test article that could reasonably infer causality. Causality should only be considered for the experimental test article and not for any standard study examination or diagnostic procedures. The four attribution categories are: Unrelated—Does not follow a reasonable temporal sequence from the administration of study drug. The event or laboratory test abnormality is clearly due to extraneous causes (disease, other drugs, environment, etc.) Unlikely related—Does not follow a known pattern of response to study drug. Does not follow a reasonable temporal sequence from the administration of study drug. Disease or other drugs provides plausible explanation.

It does not reappear or worsen when study drug is re-administered Possibly related—Follows a known pattern of response to study drug. Time sequence from administration of the study drug is reasonable. Could also be explained by disease or other drugs. Probably related—Follows a known pattern of response to study drug. Time sequence from administration of the study drug is reasonable. Response to withdrawal clinically reasonable. Cannot be reasonably explained by the known characteristics of the participant's clinical state, environmental factors, or other therapies administered to the subject.

Serious Adverse Event Reporting

All SAEs (defined herein), whether judged related or not to study medication, will be reported to the Sponsor (or designated Medical Monitor) by telephone, e-mail or facsimile within 24 hours of the Investigator becoming aware of such SAEs. The contact details can be found of the serious adverse event form.

The initial SAE Report should include, at a minimum, the following information: Protocol number; Site number; Subject screening number, initials, gender, and date of birth; Name of PI and investigator site address; Details of SAE; Criterion for classification as "serious"; Date of SAE onset.

Follow-up SAE reports should be submitted as further information becomes available, and the final SAE Report should include information on the SAE intensity, outcome, and relationship to study drug; dates of study drug administration, concomitant medications, and any other relevant information. The PI should also provide clear copies of supporting documents as necessary (e.g. hospital discharge summary, laboratory reports, autopsy reports, etc.), with the subject's personal identifiers removed. All SAEs will be followed until the acute event has resolved, even if the subject discontinues study participation prior to the resolution. The Investigator must report SAEs occurring at his/her site to the IRB/IEC as required.

Expected Adverse Events

Expected AE Related to the Test Article:

No ocular or systemic AE related to the investigational drug are expected at the doses proposed in this protocol.

Expected AE Related to the IVT Injection Procedure:

Mild discomfort related to the injection procedure (including use of an eyelid speculum, anaesthetic drops, mydriatic drops, antibiotic drops, povidone-iodine drops or flush and subconjunctival injection of anaesthetic, as well as the actual insertion of the IVT needle) are expected. These procedure-related adverse events include but are not limited to: redness, mild eye pain, eye irritation, visual disturbance, abnormal sensation in the eye, etc. and will be graded as indicated herein Disease Progression A condition considered by the PI as unequivocal AMD disease progression in the study eye or fellow eye should be identified as such in the participant's source documents and should not be recorded as an adverse event in the CRF, such as lesion growth, lesion bleeding, lesion that exudes fluid, an RPE tear, and extensive deposition of lipid. All other conditions should be recorded as an adverse event. The unequivocal nature of the disease progression must be indicated in the source documents. Normal progression or worsening of the medical condition under study (e.g. vision loss due to the progression of AMD), by itself, does not necessarily constitute an adverse event unless the change can be reasonably attributed to an action of the test article and not only to its lack of efficacy.

Withdrawal

Participants may choose to withdraw from this study for any reason at any time without penalty or prohibition from enrolling in other clinical protocols.

Participant wishing to withdraw from the study completely will be offered an early termination visit.

This early termination visit will include the examinations outlined herein.

Pregnancy in the Clinical Trial

WOCBP are not excluded from the study as long as adequate birth control methods are being utilized. Prior to enrolment in the clinical trial, WOCBP must be advised of the importance of avoiding pregnancy during the trial and the potential risks associated with an unintentional pregnancy. WOCBP and males with partners who are WOCBP will be instructed to practice an acceptable method of birth control (as defined above) for the duration of the study. Male subjects will be counselled to avoid donating sperm after dosing on Day 1 until the final Exit visit.

During the trial, female subjects are to be instructed to contact the Investigator immediately if they suspect they might be pregnant. The study Sponsor must be contacted immediately and a decision will be made regarding continuation of the pregnant woman in the study based upon the circumstances surrounding the pregnancy. Pregnancy is not reportable as an adverse event; however, complications may be reportable. If a female subject or partner of a male subject becomes pregnant during the study, the PI should report the pregnancy to the Medical Monitor within 24 hours of being notified. The Investigator should follow the pregnancy until completion. At the completion of the pregnancy, the Investigator will document and report the outcome. If the outcome of the pregnancy meets the criteria for classification as an SAE (i.e. postpartum complication, stillbirth, neonatal death, or congenital anomaly) the Investigator should follow the procedures for reporting an SAE.

Statistical Considerations

Descriptive summaries will include mean, standard deviation, median, and range for continuous variables and counts and percentages for categorical variables.

Population for Analysis

Safety Analysis: All subjects who received at least one dose of treatment will be included in the evaluation of safety of FCA.

Efficacy Endpoint(s): The efficacy analysis will be based on an intention-to-treat population (ITT), which is defined as all subjects who received the single dose of treatment and have at least one visit at or after month 2. Month 2 is the first visit on treatment at which lesion area is measured. Per protocol (PP) efficacy analyses will include all randomized subjects who return for Day 150 of follow up.

Safety is the main analysis population for safety endpoints, and ITT is the main analysis population for efficacy endpoints. The assignment of participants to each analysis population will be based on the review of data after the completion of all data collection, monitoring by the clinical research associate and first round of query resolution by data management and prior to database lock.

Demographic and Baseline Characteristics

Participant demographic and baseline variables (age, sex, ethnicity, race, height, weight, and BMI) will be summarised with descriptive statistics. Sex, ethnicity, and race will be summarised with frequency counts and percentages. Baseline ocular assessments will be summarised descriptively as well.

Pregnancy test results, concomitant medication and medical history data for each participant will be presented in data listings. Concomitant medications will be summarised descriptively by using frequency counts and percentages.

Analysis of Primary Safety Endpoints

No formal inferential statistics will be performed on safety assessments. Statistical methods for the safety analyses will be primarily descriptive in nature. The Fludrocortisone acetate 1 mg/0.1 mL and 2 mg/0.1 mL injection will be considered as safe and tolerable based on the number of subjects presenting severe AEs related to the study drug. It is understood that safety is a medical judgment that cannot be prospectively defined in detail. However, as general guidance, a subject will be considered to have tolerated a dose if the subject experiences no clinically significant drug-related adverse event or laboratory abnormality. Conversely, a subject will not be considered to have tolerated the dose if he experiences a clinically significant drug-related adverse event or laboratory abnormality during the study drug administration or post-administration follow-up period.

Listings and summaries for all safety data will be presented using the Safety Population. Descriptive statistics (mean, SD, median, minimum and maximum) will be calculated for summaries of continuous safety data and frequency counts and percentages (where appropriate) will be calculated for summaries of discrete/categorical safety data.

Adverse events (AEs) will be coded using the Medical Dictionary for Regulatory Activities (MedDRA), and data will be summarised by System, Organ, Class and preferred term. The number and percent of participants reporting each AE will be summarised descriptively (n=9). A participant with two or more AEs within the same level of summarisation (i.e., system, organ, class or preferred term) will be counted only once in that level. The number of AEs reported will also be presented. Adverse events will also be summarised by severity as well as relationship to study treatment. A by-participant AE data listing, including verbatim term, preferred term, system organ class, severity, and relationship to study treatment, will be provided. Separate listings will be generated for SAEs and AEs leading to study/treatment discontinuation.

All haematology, blood chemistry and urinalysis (continuous variables) parameters will be summarised using descriptive statistics for all study visits assessed, including change from baseline (last pre-surgery value) for all post-surgery assessments. All laboratory data will be included in the data listings and all test values outside the normal range will be flagged.

All vital sign parameters will be summarised using descriptive statistics by study visit, including change from baseline (last pre-surgery) for all post-surgery assessments.

Individual vital sign assessments will be listed for each participant. Findings of physical examinations will be listed for each participant and summarised descriptively by using count and percentage by study visit.

Analysis of Secondary Endpoints

The efficacy endpoints are the secondary endpoints of this study, which include complete ocular examination.

ETDRS best-corrected visual acuity (BCVA) will be scored with reference to the Early Treatment Diabetic Retinopathy Study ETDRS letters). ETDRS will be treated as continuous data, and descriptive statistics (mean, SD, median, minimum and maximum) will be summarised for ETDRS observed value and change from baseline at each post-surgery visit. Exploratory analysis of ETDRS change over time will be assessed by using a mixed model. The correlations between repeated measures of the same participant will be accounted for by the mixed model. The least squares mean of ETDRS change from baseline and its 95% confidence interval at each visit will be estimated. Similar analyses will be conducted for intraocular pressures. Categorical efficacy endpoints such as slit lamp biomicroscopy exam findings, dilated ophthalmoscopy exam findings, color fundus photography and OCT finding will be summarised descriptively by frequency count and percentage (proportion) where appropriate.

Interim Analysis

There is no formal interim analysis planned for this study.

Sample Size

The study is planned to enroll up to 12 participants.

The sample size chosen for this study was selected without formal statistical justification, but the numbers chosen are considered adequate for assessing the study objectives. The sample size was determined on the basis of practical and logistical considerations and not based on statistical power with regard to hypothesis testing or precision with regard to parameter estimation.

This phase 1 trial was designed to identify any important limiting toxicities and to determine if this dose is suitable for phase 2 trial. This was also designed to minimize the likelihood that a minimum number of subjects will be exposed to the investigational drug.

This is an open label study, and no randomization is conducted in this study.

Missing Data

Missing data will generally not be imputed for safety or efficacy data.

Data Collection, Retention and Monitoring

Data Collection Instruments

The investigator will prepare and maintain adequate and accurate source documents designed to record all observations and other pertinent data for each participant treated with the study drug.

Study personnel at each site will enter data from source documents corresponding to a participant's visit into the protocol-specific electronic Case Report Form (eCRF) when the information corresponding to that visit is available. Participants will not be identified by name in the study database or on any study documents to be collected by the Sponsor (or designee), but will be identified by a site number, participant number and initials.

If a correction is required for an eCRF, the time and date stamps track the person entering or updating eCRF data and creates an electronic audit trail. The Investigator is responsible for all information collected on participants enrolled in this study. All data collected during the course of this study must be reviewed and verified for completeness and accuracy by the Investigator. A copy of the CRF will remain at the Investigator's site at the completion of the study.

Data Management Procedures

The data will be entered into a validated database. The Data Management group will be responsible for data processing, in accordance with procedural documentation. Database lock will occur once quality assurance procedures have been completed.

All procedures for the handling and analysis of data will be conducted using good computing practices meeting FDA guidelines for the handling and analysis of data for clinical trials.

Data Quality Control and Reporting

After data have been entered into the study database, a system of computerised data validation checks will be implemented and applied to the database on a regular basis.

Queries are entered, tracked, and resolved through the EDC system directly. The study database will be updated in accordance with the resolved queries. All changes to the study database will be documented.

Archival Data

The database is safeguarded against unauthorised access by established security procedures; appropriate backup copies of the database and related software files will be maintained. Databases are backed up by the database administrator in conjunction with any updates or changes to the database.

At critical junctures of the protocol (e.g., production of interim reports and final reports), data for analysis is locked and cleaned per established procedures.

Availability and Retention of Investigational Records

The Investigator must make study data accessible to the monitor, other authorized representatives of the Sponsor (or designee), IRB/IEC, and Regulatory Agency (e.g., FDA, TGA) inspectors upon request. A file for each participant must be maintained that includes the signed informed Consent, HIPAA Authorization and Assent Form and copies of all source documentation related to that participant. The Investigator must ensure the reliability and availability of source documents from which the information on the eCRF was derived.

All study documents (patient files, signed informed consent forms, copies of eCRFs, Study File Notebook, etc.) must be kept secured for a period of fifteen years following the completion of the study.

Monitoring

Monitoring visits will be conducted by representatives of the Sponsor according to the U.S. CFR Title 21 Parts 50, 56, and 312 and ICH Guidelines for GCP (E6). By signing this protocol, the investigator grants permission to the Sponsor (or designee), and appropriate regulatory authorities to conduct on-site monitoring and/or auditing of all appropriate study documentation.

Data Safety Monitoring Board

An independent DSMB will be convened. The mission of the DSMB will be to ensure the ethical conduct of the trial and to protect the safety interests of patients in this study.

The DSMB will be responsible for reviewing the cumulative safety results from the study. The DSMB will meet prior to the commencement of the study, and will review all available safety/tolerability data (e.g., adverse events, serious adverse events, clinical laboratory assessments, blood pressure, haematology, urology) at Day 0 and 1 month after IVT injection of FCA of the initial participant in Part 1 and 3 (prior to Part 2 & 4 of the study), and convene as required throughout the study period to review data and potential safety risks. The criteria for evaluating study continuation will relate to study safety, including the incidence and severity of ocular and/or systemic side effects not limited to but including; change in IOP of >10 mmHg, a loss of 15 letters or more in BCVA, presence or intraocular inflammation, presence or absence of ocular pain, change in BP of 30 mmHg (systolic or diastolic), incidence of hospitalisation or systemic illness, and any other ocular or systemic adverse events reported. Any changes will be referenced to baseline measurements. The DSMB will then meet at the conclusion of the study and after the final statistical analysis in order to review all data.

DSMB will consist an ophthalmologist, and a biostatistician, both independent of the study team.

Participant Confidentiality

In order to maintain participant confidentiality, only a site number, participant number and participant initials will identify all study participants on eCRFs and other documentation submitted to the Sponsor. Additional participant confidentiality issues (if applicable) are covered in the Clinical Study Agreement.

Administrative, Ethical, Regulatory Considerations

The study will be conducted according to the Declaration of Helsinki, Protection of Human Volunteers (21 CFR 50), Institutional Review Boards (21 CFR 56), and Obligations of Clinical Investigators (21 CFR 312).

To maintain confidentiality, all laboratory specimens, evaluation forms, reports and other records will be identified by a coded number and initials only. All study records will be kept in a locked file cabinet and code sheets linking a patient's name to a patient identification number will be stored separately in another locked file cabinet. Clinical information will not be released without written permission of the participant, except as necessary for monitoring by the TGA. The Investigator must also comply with all applicable privacy regulations (e.g., The Health Records and Information Privacy Act 2002).

Protocol Amendments

Any amendment to the protocol will be written by the Sponsor. Protocol amendments cannot be implemented without prior written IRB/IEC approval except as necessary to eliminate immediate safety hazards to patients. A protocol amendment intended to eliminate an apparent immediate hazard to patients may be implemented immediately, provided the IRBs are notified within five working days.

Institutional Review Boards and Independent Ethics Committee

The protocol and consent form will be reviewed and approved by the IRB/IEC of each participating centre prior to study initiation. Serious adverse events regardless of causality will be reported to the IRB/IEC in accordance with the standard operating procedures and policies of the IRB/IEC, and the Investigator will keep the IRB/IEC informed as to the progress of the study. The Investigator will obtain assurance of IRB/IEC compliance with regulations.

Any documents that the IRB/IEC may need to fulfil its responsibilities (such as protocol, protocol amendments, Investigator's Brochure, consent forms, information concerning patient recruitment, payment or compensation procedures, or other pertinent information) will be submitted to the IRB/IEC. The IRB/IECs written unconditional approval of the study protocol and the informed consent form will be in the possession of the Investigator before the study is initiated. The IRB/IECs unconditional approval statement will be transmitted by the Investigator to the Sponsor or designee prior to the shipment of study supplies to the site. This approval must refer to the study by exact protocol title and number and should identify the documents reviewed and the date of review.

Protocol and/or informed consent modifications or changes may not be initiated without prior written IRB/IEC approval except when necessary to eliminate immediate hazards to the patients or when the change(s) involves only logistical or administrative aspects of the study. Such modifications will be submitted to the IRB/IEC and written verification that the modification was submitted and subsequently approved should be obtained.

The IRB/IEC must be informed of revisions to other documents originally submitted for review; serious and/or unexpected adverse events occurring during the study in accordance with the standard operating procedures and policies of the IRB; new information that may affect adversely the safety of the patients of the conduct of the study; an annual update and/or request for re-approval; and when the study has been completed.

Informed Consent Form (ICF)

Informed consent will be obtained in accordance with the Declaration of Helsinki, ICH GCP, US Code of Federal Regulations for Protection of Human Subjects (21 CFR 50.25 [a,b], CFR 50.27, and CFR Part 56, Subpart A), the Health Insurance Portability and Accountability Act (HIPAA, if applicable), and local regulations.

The present invention is of significant advantage because the improved physicochemical property may improve the required course of therapy for example, in reducing the number of intraocular injections required or increasing the period between intraocular injections and/or improve the ease of injection.

Additionally, the present invention is of significant advantage because the decreased number of injections or increased period between objections may lead to increased patient compliance. This in turn will lead to improved ocular health outcomes.

This present invention is of particular advantage over prior art multi-dose formulations which result in significant waste when regulations only allow one use of a multi-dose vial. Additionally, the pre-filled syringe is convenient for the health-care provider performing the injection and it's ease of handling may reduce error.

The tailored, single unit dose of the present claimed invention is safer, more cost effective and more accurate than conventional multi-dose formulations.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

TABLE 1

Mineralocorticoid Receptor and Glucocorticoid Receptor activity of some corticosterones

| Compound | GR potency | MR potency | Duration of action ($t_{1/2}$ in hours) |
|---|---|---|---|
| Hydrocortisone (cortisol) | 1 | 1 | 8 |
| Cortisone | 0.8 | 0.8 | oral 8; i.m. 18+ |
| Prednisone | 3.5-5 | 0.8 | 16-36 |
| Prednisolone | 4 | 0.8 | 16-36 |
| Methylprednisolone | 5-7.5 | 0.5 | 18-40 |
| Dexamethasone | 25-80 | 0 | 36-54 |
| Betamethasone | 25-30 | 0 | 36-54 |
| Triamcinolone | 5 | 0 | 12-36 |
| Beclometasone | 8 puffs 4 times a day; equals 14 mg oral prednisone once/day | — | — |
| Fludrocortisone acetate | 15 | 200 | 24 |
| Deoxycorticosterone acetate (DOCA) | 0 | 20 | — |
| Aldosterone | 0.3 | 200-1000 | — |

Key:
MR = mineralocorticoid receptor;
GR = glucocorticoid receptor;
i.m. intramuscular

TABLE 2

Measure Particle Size Distribution

| Drug | D(v, 0.5) microns | D(v, 0.9) microns |
|---|---|---|
| 11-DC | 81 | 233 |
| DCS | 22 | 80 |
| DCSA | 52 | 226 |
| FLU | 4 | 10 |
| TA | 5 | 11 |

TABLE 3

Suspension of compounds

| Suspension with CMC and Tween 80 | | | Suspension without CMC and Tween 80 | | |
|---|---|---|---|---|---|
| Suspension quality | Drawing-up | Expelling | Suspension quality | Drawing-up | Expelling |
| Homogenous suspension, No flocculation or layer Separation | Easy to draw-up all formulation (Excellent) | Easy to expel (Excellent) | Two layers obviously Separated 1- Top transparent liquid layer (water) 2- Bottom white solid layer (particles) | Easy to draw-up but you may need to shake very well before drawn | Easy to expel |
| Homogenous suspension, No flocculation or layer Separation | Easy to draw-up all formulation (Excellent) | Easy to expel (Excellent) | Two layers obviously separated 1- Top transparent liquid layer (water) 2- Bottom white solid layer (particles) | Easy to draw-up but you may need to shake very well before drawn | Easy to expel |

TABLE 3-continued

Suspension of compounds

| Suspension with CMC and Tween 80 | | | Suspension without CMC and Tween 80 | | |
|---|---|---|---|---|---|
| Suspension quality | Drawing-up | Expelling | Suspension quality | Drawing-up | Expelling |
| Homogenous suspension, No flocculation or layer Separation | Easy to draw-up all formulation (Excellent) | Easy to expel (Excellent) | Two layers obviously separated 1- Top foamy white layer (particles) 2- Bottom liquid transparent (water) | Easy to draw-up, but not all formulation up because of homogeneity | Easy to expel |
| Homogenous suspension No flocculation or layer separation | Easy to draw-up all formulation (Excellent) | Easy to expel (Excellent) | Homogenous suspension No flocculation or layer separation | Easy to draw-up all formulation | Easy to expel |
| Homogenous suspension, No flocculation or layer separation | Easy to draw-up all formulation (Excellent) | Easy to expel (Excellent) | Two layers obviously separated 1- Top foamy white layer (particles) 2- Bottom liquid transparent (water) | Easy to draw-up, but not all formulation up because of homogeneity | Easy to expel |

TABLE 4

Formulation Utilized
Component Function Mass (ml)

Tween 80 Wetting agent 0.4 mg
CMC Viscosity modifier 12.5 mg
Drug Active 40 mg

TABLE 5

Summary of batch production results
indicating applicability of method

Drug
11-DC
Test Method ID Specification Result Date tested Comments

Av Drug RGA40/1 20.0 ± 2.0 mg 18.4 ± 0.5 27 Oct. 2006 Passed
Content per vial
Particle RGA40/2 D(0.5) = <20 7.1 3 Nov. 2006 Passed
Size D(0.9) = <30 25
pH RGA40/3 6.0-8.0 7.0 3 Nov. 2006 Passed
DCS
Test Method ID Specification Result Date tested Comments Av Drug RGA40/1 20.0 ± 2.0 mg 18.5 ± 0.7 1 Nov. 2006 Passed
Content per vial
Particle RGA40/2 D(0.5) = <20 12.7 3 Nov. 2006 Passed
Size D(0.9) = <30 30.0
pH RGA40/3 6.0-8.0 7.0 3 Nov. 2006 Passed
DCSA
Test Method ID Specification Result Date tested Comments Av Drug RGA40/1 20.0 ± 2.0 mg 16 ± 0.9 2 Nov. 2006 Failed•
Content per vial
Particle RGA40/2 D(0.5) = <20 8.25 3 Nov. 2006 Passed
Size D(0.9) = <30 26.77
pH RGA40/3 6.0-8.0 7.0 3 Nov. 2006 Passed
Fludra
Test Method ID Specification Result Date tested Comments Av Drug RGA40/1 20.0 ± 2.0 mg 18.1 ± 0.7 25 Oct. 2006 Passed
Content per vial
Particle RGA40/2 D(0.5) = <20 3.47 3 Nov. 2006 Passed
Size D(0.9) = <30 9.16
pH RGA40/3 6.0-8.0 7.0 3 Nov. 2006 Passed
T.A
Test Method ID Specification Result Date tested Comments Av Drug RGA40/1 20.0 ± 2.0 mg 18.33 ± 0.7 30 Oct. 2006 Passed
Content per vial
Particle RGA40/2 D(0.5) = <20 4.43 3 Nov. 2006 Passed
Size D(0.9) = <30 8.57
pH RGA40/3 6.0-8.0 7.0 3 Nov. 2006 Passed

TABLE 6

Composition of Triesecence

| Triamcinolone acetonide | 40 mg/mL |
|---|---|
| carboxymethylcellulose sodium | 0.5% w/v; 5 mg/mL |
| polysorbate 80 | 0.015% (not stipulated but expect w/v = 1.5 mg/mL |
| sodium chloride | to isotonic |
| potassium chloride, calcium chloride (dehydrate), magnesium chloride (hexahydrate), sodium acetate (trihydrate), sodium citrate (dihydrate) | levels not stipulated, but suspect BSS composition?? |
| hydrochloric acid and/ or sodium hydroxide | for pH adjustment |
| Water for injection | Qs |

TABLE 7

Kenalog Composition

| Triamcinolone acetonide | 10 mg/mL |
|---|---|
| carboxymethylcellulose sodium | 0.75% w/v; 7.5 mg/mL |
| polysorbate 80 | 0.04% (not stipulated but expect w/v = 0.4 mg/mL |
| sodium chloride | 0.65% to isotonic |
| benzyl alcohol | 0.9% (w/v) |
| hydrochloric acid and/or sodium hydroxide | for pH adjustment |
| Water for injection | qs |

TABLE 8

Schedule of Activities

| Procedures | Screening Day −14 to −1 | Baseline Visit 1, Day 0 | Study Visit 2 Day 1 +/− 1 day | Study Visit 3 Day 7 +/− 1 day | Study Visit 4 Day 14 +/− 1 day | Study Visit 5 Day 28 +/− 1 day | Study Visit 6 Day 60 +/− 1 day | Study Visit 7 Day 90 +/− 1 day | Final Study Visit 8 Day 150 +/− 1 day |
|---|---|---|---|---|---|---|---|---|---|
| Informed consent | X | | | | | | | | |
| Demographics | X | | | | | | | | |
| Medical history | X | | | | | | | | |
| Concomitant Medications | X | X | X | X | X | X | X | X | X |
| Adverse event review | | | X | X | X | X | X | X | X |
| Administer study intervention | | X | | | | | | | |
| Physical exam | X | X | | | X | | | X | X |
| Vital signs | X | X | X | X | X | X | X | X | X |
| Best corrected visual acuity (BCVA) | X | X | X | X | X | X | X | X | X |
| Height and Weight | X | | | | | | X | | X |
| Visual Function Questionnaire (VFQ-25) | | X | | | | | | | X |
| Goldmann Intraocular Pressure (IOP) | X | X | X | X | X | X | X | X | X |
| Slit lamp biomicroscopy, incl. lens grading | X | X | X | X | X | X | X | X | X |
| Dilated ophthalmoscopy | X | X | X | X | X | X | X | X | X |
| SD-OCT | X | X | X | X | X | X | X | X | X |
| FAF and NIFR | X | X | X | X | X | X | X | X | X |
| Colour Fundus Photography | X | | | | | | X | | X |
| Fluorescein angiogram | X | | | | | | | | X |
| Haematology & Urinalysis | X | X | | X | | X | | | X |
| Serum chemistry[a] | X | X | | X | | X | | | X |
| Urine Pregnancy test[b] | X | | | | | | | | X |
| Pharmacokinetic sampling | | X | | X | | X | | | X |
| Complete Case Report Forms (CRFs) | X | X | X | X | X | X | X | X | X |

[a] Albumin, alkaline phosphatase, total bilirubin, bicarbonate, BUN, calcium, chloride, creatinine, glucose, LDH, phosphorus, potassium, total protein, AST, ALT, sodium.
[b] Serum pregnancy test (women of childbearing potential).

TABLE 9

| | Treatment Arm | Dose Escalation |
|---|---|---|
| Part 1 | Fludrocortisone acetate 1 mg/0.1 mL at Day 0 | If no dose limiting toxicity is observed in 3 patients at this given dose level, the dose will be escalated to the following level: |
| Part 2 | Fludrocortisone acetate 2 mg/0.1 mL at Day 0 | |

TABLE 10

| Assay | Number of Time Points | Approximate Volume per Time Point (mL) | Approximate Sample Volume Over Course of Study (mL) |
|---|---|---|---|
| Pharmacokinetics | 4/9 | 4 | 36 |
| Haematology | 5/9 | 4 | 36 |
| Chemistry (Incl. HCG/LH/FSH) | 5/9 | 8.5 | 76.5 |

The invention claimed is:

1. A unit dose pharmaceutical composition comprising:
   2.0 to 8.0 mg of a reconstitutable dry powder of fludrocortisone acetate and/or triamcinolone acetonide;
   wherein the unit dose pharmaceutical composition is comprised in a syringe.

2. The unit dose pharmaceutical composition of claim 1 further comprising:
   0.6 to 0.75% (w/v) of carboxy methyl cellulose (CMC); and
   0.015 to 0.04 (w/v) of a surfactant.

3. The unit dose pharmaceutical composition of claim 1 wherein the syringe comprises a 25 to 30 gauge.

4. The unit dose pharmaceutical composition of claim 1 wherein the syringe comprises a volume of 0.25 to 0.75 ml.

5. The unit dose pharmaceutical composition of claim 1 wherein the syringe is a double-barrelled syringe.

6. The unit dose pharmaceutical composition according to claim 5, wherein a first barrel comprises the unit dose pharmaceutical composition and a second barrel comprises another medicament.

7. The unit dose pharmaceutical composition according to claim 1, wherein the volume of the pharmaceutical composition comprised in the syringe is 0.05 to 0.15 ml.

8. The unit dose pharmaceutical composition according to claim 1, wherein the fludrocortisone acetate or triamcinolone acetonide is comprised in at least two particle sizes.

9. The unit dose pharmaceutical composition according to claim 1, wherein the pharmaceutical composition comprises a viscosity of 2 to 15 cps.

10. The unit dose pharmaceutical composition according to claim 1, wherein the pharmaceutical composition comprises a degree of flocculation of about 9.5 or greater.

11. The unit dose pharmaceutical composition-according to claim 1 comprising fludrocortisone acetate and triamcinolone acetonide.

12. The unit dose pharmaceutical composition according to claim 1, wherein the pharmaceutical composition is preservative free.

13. The unit dose pharmaceutical composition according to claim 1, wherein the fludrocortisone acetate or triamcinolone acetonide is capable of modulating the activity of both a mineralocorticoid receptor and a glucocorticoid receptor.

14. The unit dose pharmaceutical composition according to claim 1 further comprising hemp seed oil.

* * * * *